United States Patent
Oka et al.

(10) Patent No.: US 10,744,030 B2
(45) Date of Patent: Aug. 18, 2020

(54) HEATING IMPLEMENT

(71) Applicant: KAO CORPORATION, Tokyo (JP)

(72) Inventors: Takeshi Oka, Funabashi (JP); Yasuto Saita, Setagaya-ku (JP); Katsutoshi Hara, Utsunomiya (JP)

(73) Assignee: KAO CORPORATION, Tokyo (JP)

(*) Notice: Subject to any disclaimer, the term of this patent is extended or adjusted under 35 U.S.C. 154(b) by 1092 days.

(21) Appl. No.: 14/897,189

(22) PCT Filed: Jun. 10, 2014

(86) PCT No.: PCT/JP2014/065353
§ 371 (c)(1),
(2) Date: Dec. 9, 2015

(87) PCT Pub. No.: WO2014/199986
PCT Pub. Date: Dec. 18, 2014

(65) Prior Publication Data
US 2016/0128866 A1    May 12, 2016

(30) Foreign Application Priority Data

Jun. 10, 2013  (JP) ................. 2013-121733

(51) Int. Cl.
*A61F 7/03* (2006.01)
*F24V 30/00* (2018.01)
(Continued)

(52) U.S. Cl.
CPC ............. *A61F 7/034* (2013.01); *A61M 21/02* (2013.01); *F24V 30/00* (2018.05);
(Continued)

(58) Field of Classification Search
CPC .... A61F 2007/0226; A61F 2007/0258; A61M 2205/364
See application file for complete search history.

(56) References Cited

U.S. PATENT DOCUMENTS 6,096,067 A * 8/2000 Cramer ................. A61F 7/03
607/108
6,336,935 B1   1/2002 Davis et al.
(Continued)

FOREIGN PATENT DOCUMENTS

CA    2 830 152 A1   10/2012
CN    101732123 A    6/2010
(Continued)

OTHER PUBLICATIONS

Combined Chinese Office Action and Search Report dated Jul. 20, 2016 in Patent Application No. 201480033176.5 (with partial English language translation and English translation of categories of cited documents).
(Continued)

*Primary Examiner* — Avinash A Savani
*Assistant Examiner* — Deepak A Deean
(74) *Attorney, Agent, or Firm* — Oblon, McClelland, Maier & Neustadt, L.L.P.

(57) ABSTRACT

A heating implement (1) for body of the present embodiment includes a first sheet (11) having air-permeability; a second sheet (12); a heating element (13), intermediately arranged between the first sheet (11) and the second sheet (12) and containing an oxidizeable metal and a carbon component; and a first adhesive layer (14) and a second adhesive layer (15) provided in one of external surfaces of the first sheet (11) which is applied to a wearer side, in which a region without adhesive layer, in which none of the first adhesive layer (14) and the second adhesive layer (15) is disposed, is provided in at least a part of an external circumference section of the first sheet (11), the following relations (a) and (b) are satisfied, and the heating implement is perfumed with a fragrance:
(a) a mass ratio of a content of the fragrance to a content of the carbon component in the aforementioned heating imple-
(Continued)

ment (fragrance/carbon component) is equal to or higher than 0.2 and equal to or lower than 0.52; and (b) the content of the carbon component in the aforementioned heating implement is equal to or larger than 0.89 mg/cm$^2$.

20 Claims, 7 Drawing Sheets

(51) Int. Cl.
  *A61M 21/02* (2006.01)
  *A61F 7/02* (2006.01)
  *A61M 21/00* (2006.01)

(52) U.S. Cl.
  CPC .......... *A61F 2007/0226* (2013.01); *A61F 2007/0258* (2013.01); *A61M 2021/0016* (2013.01); *A61M 2021/0066* (2013.01); *A61M 2205/364* (2013.01); *A61M 2209/088* (2013.01)

(56) References Cited

U.S. PATENT DOCUMENTS

| | | | | |
|---|---|---|---|---|
| 2004/0035410 | A1* | 2/2004 | Igaki | A61F 7/03 126/263.05 |
| 2004/0042965 | A1* | 3/2004 | Usui | A61F 7/034 424/40 |
| 2004/0149732 | A1 | 8/2004 | Usui et al. | |
| 2004/0244413 | A1* | 12/2004 | Trinh | A61F 7/103 62/530 |
| 2005/0192653 | A1* | 9/2005 | Tsunakawa | A61F 7/034 607/109 |
| 2008/0289616 | A1* | 11/2008 | Ohnishi | A61F 7/034 126/263.01 |
| 2010/0198325 | A1* | 8/2010 | Ishikawa | A61F 7/034 607/112 |
| 2010/0241199 | A1* | 9/2010 | Hidaka | A61F 7/034 607/96 |
| 2011/0076430 | A1* | 3/2011 | Shigematsu | C09J 7/38 428/35.2 |
| 2011/0190714 | A1 | 8/2011 | Oda et al. | |
| 2013/0079851 | A1 | 3/2013 | Tagami et al. | |
| 2013/0125837 | A1 | 5/2013 | Ueno et al. | |
| 2014/0031748 | A1 | 1/2014 | Usui | |
| 2014/0345543 | A1 | 11/2014 | Saita et al. | |
| 2014/0345595 | A1* | 11/2014 | Nishioka | A61F 7/034 126/263.01 |
| 2014/0373828 | A1 | 12/2014 | Oka | |
| 2019/0142628 | A1* | 5/2019 | Igaue | A61F 7/034 607/108 |
| 2020/0046550 | A1* | 2/2020 | Igaue | A61K 9/70 |

FOREIGN PATENT DOCUMENTS

| | | |
|---|---|---|
| CN | 101778611 A | 7/2010 |
| CN | 102227198 A | 10/2011 |
| CN | 102946832 A | 2/2013 |
| CN | 102988128 A | 3/2013 |
| EP | 1 147 752 B1 | 10/2001 |
| EP | 1 577 363 A1 | 9/2005 |
| EP | 1 707 165 A1 | 10/2006 |
| EP | 2 177 184 A1 | 4/2010 |
| JP | 07-284507 A | 10/1995 |
| JP | 2000-260 A | 1/2000 |
| JP | 2001-187727 A | 7/2001 |
| JP | 2003-509120 A | 3/2003 |
| JP | 2003-135509 A | 5/2003 |
| JP | 2008-029743 A | 2/2008 |
| JP | 2010-051690 A | 3/2010 |
| JP | 2010-284340 A | 12/2010 |
| JP | 2011-135944 A | 7/2011 |
| JP | 2011-160885 A | 8/2011 |
| JP | 5031135 B2 | 7/2012 |
| JP | 2013-42963 A | 3/2013 |
| JP | 2013-070945 A | 4/2013 |
| JP | 2013-146554 A | 8/2013 |
| JP | 2013-146555 A | 8/2013 |
| JP | 2013-176549 A | 9/2013 |
| JP | 2013-252320 A | 12/2013 |
| JP | 2013-252328 A | 12/2013 |
| RU | 65 756 U1 | 8/2007 |
| WO | WO 2011/155542 A1 | 12/2011 |
| WO | WO 2012/140875 A1 | 10/2012 |

OTHER PUBLICATIONS

Combined Office Action and Search Report dated Mar. 12, 2018 in Russian Patent Application No. 2015156118 (with English language translation).
International Search Report dated Sep. 22, 2014 for PCT/JP2014/065353 filed on Jun. 10, 2014.
Extended European Search Report dated Dec. 15, 2016 in Patent Application No. 14810721.2.
Japanese Office Action dated Jan. 9, 2018, in Japanese Patent Application No. 2014-119767, 4 pages.
Office Action and Search Report dated Jul. 8, 2016 in the corresponding Singapore Patent Application No. 11201509664Y (with English Translation).

* cited by examiner

HEATING IMPLEMENT

TECHNICAL FIELD

The present invention relates to a heating implement for a body.

BACKGROUND OF THE INVENTION

In recent years, heating implements, which are capable of generating heat through oxidation reactions of oxidizeable metals, are used. Heating implements that are perfumed with fragrances among the above-described types of the heating implements have been developed, in order to induce a relaxing feel, a refreshing feel, an initiation of sleep, a feel of sound sleep and the like. For example, Patent Document 1 discloses a use of a fragrance-added heating implement so as to be mated with both eyes of a wearer.

Also, Patent Document 2 describes a handy heating pad having a water-retention gel layer impregnated with an aroma oil as a type of a heating implement to be stuck on a skin.

RELATED DOCUMENTS

Patent Documents

[Patent Document 1]
Japanese Patent Application Laid-Open No. 2010-51,690
[Patent Document 2]
Japanese Patent Application Laid-Open No. 2003-135,509

SUMMARY OF THE INVENTION

According to one aspect of the invention, there is provided a heating implement for body comprising:
a first sheet having air-permeability;
a second sheet;
a heating element, intermediately arranged between the aforementioned first sheet and the aforementioned second sheet and containing an oxidizeable metal and a carbon component; and
an adhesive layer provided in one of external surfaces of the aforementioned first sheet which is applied to a wearer side,
wherein a region without adhesive layer, in which none of the aforementioned adhesive layer is disposed, is provided in at least a part of an external circumference section of the aforementioned first sheet,
wherein following relations (a) and (b) are satisfied, and
wherein the aforementioned heating implement is perfumed with a fragrance:
(a) a mass ratio of a content of the aforementioned fragrance to a content of the aforementioned carbon component in the aforementioned heating implement (fragrance/carbon component) is equal to or higher than 0.2 and equal to or lower than 0.52; and
(b) the content of the aforementioned carbon component in the aforementioned heating implement is equal to or larger than 0.89 mg/cm$^2$.

BRIEF DESCRIPTION OF THE DRAWINGS

Features and advantages of the present invention will be more apparent from the following description of certain preferred embodiments taken in conjunction with the accompanying drawings.

DETAILED DESCRIPTION OF THE INVENTION

Figure 1:
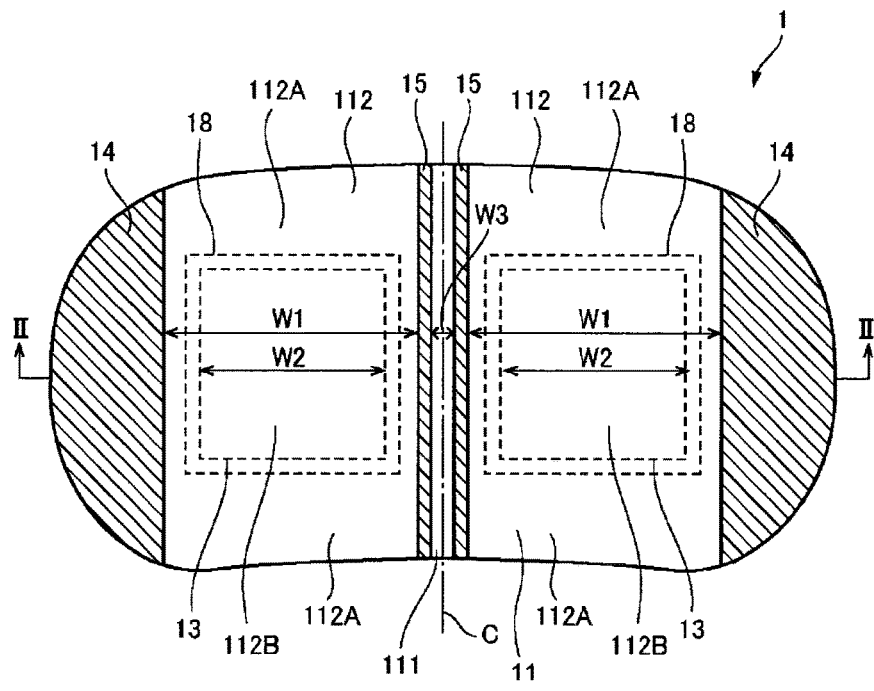
FIG. 1 is a plan view, illustrating a heating implement according to an embodiment of the present invention.

It has been revealed by studies of the present inventors for perfuming types of heating implements to be adhered to human body that scented aroma may become weak depending on a location to be put, according to the conventional perfuming quantities and perfuming methods. More specifically, while the product described in Patent Document 1 requires only small perfuming amount as it is dedicated to being applied over the eyes near the nose, the product for attaching on the side of the back of the human body requires increased perfuming amount, as compared with that for the product for being applied over the eyes. On the other hand, since the volatilization of the fragrance tends to be reduced when the fragrance component is contained in a gel as in the product of Patent Document 2, the effect of the fragrance may be similarly reduced depending on the location to be put. Therefore, the present inventors have made investigations for effectively exhibiting the effect of the fragrance by increasing the perfuming amount as compared with the conventional perfuming articles and by incorporating the fragrance in a sheet section, which exhibits easier evaporation, and neither in the adhesive layer nor in the heating element.

As results of the above-described investigations, another problem has been arisen. The investigations for the perfumed heating implement in respect to the heat generation characteristics and the adhesiveness to the wearer at the time of the use reveal that larger amount of the fragrance incorporated into the sheet is adsorbed by the carbon component in the exothermic composition and the adhesive agent for the adhesion to the body in the heating implement during the long-term storage, such that there is needs to be improved in the heat generation characteristics and the adhesive force. And on the other hand, the level of the adhesive force of the adhesive layer is limited to some extent in the case of being adhered to the body surface (skin), in terms of a need for reducing an irritation caused by the removal thereof. More specifically, increased content of the fragrance easily results in deteriorated heat generation characteristics and adhesive force, and on the other hand, increased content of the carbon component tends to provide insufficient aromas.

Further investigations have been made, and it is found that use of a specific ratio of the fragrance and the carbon component as well as a specific content of the carbon component allows providing a heating implement exhibiting better balance among the fragrance, the heat generation characteristics and the adhesive force.

According to the present invention, a heating implement for body, which is used by being attached to the body and exhibits better balance among the fragrance, the heat generation characteristics and the adhesive force, can be provided.

Exemplary implementations according to the present invention will be described in detail as follows on the basis of the annexed figures. Here, in all figures, the same numeral is referred to a similar constituent element, and the detailed description thereof will not be repeated so as to avoid duplications.

Figure 2:
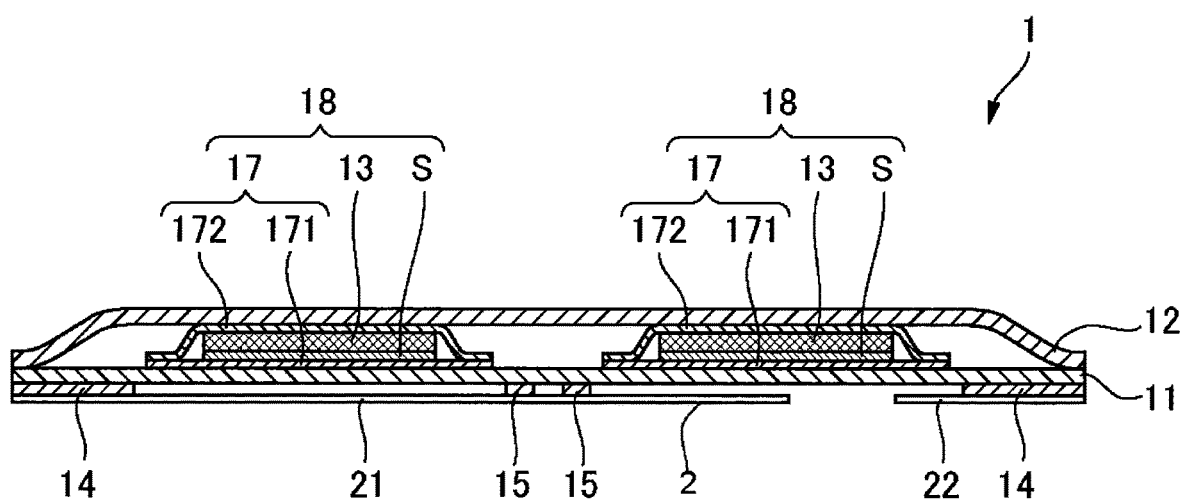
FIG. 2 is a cross-sectional view along line II-II in FIG. 1.
Figure 3:
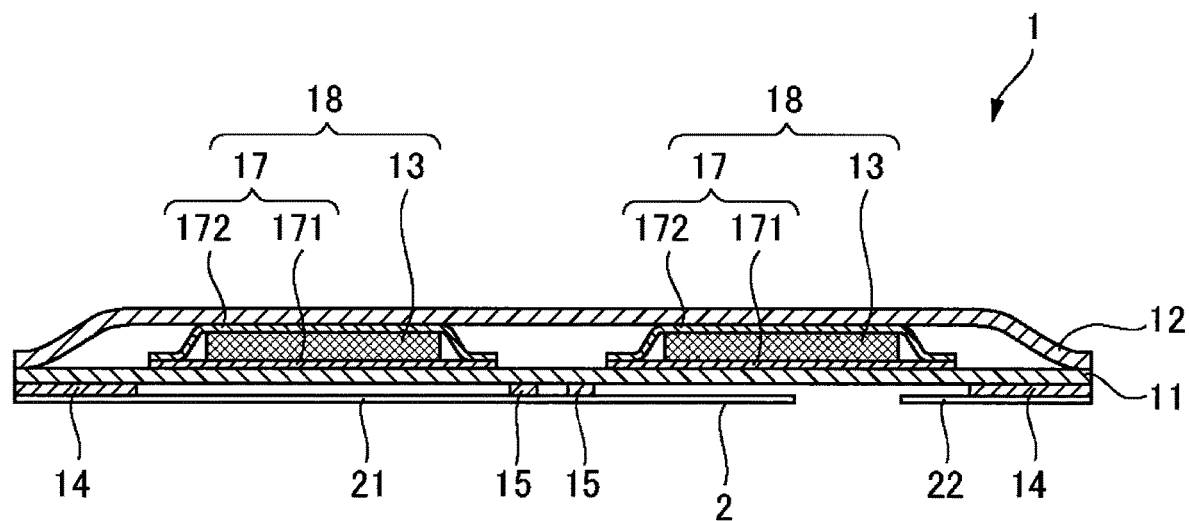
FIG. 3 is a cross-sectional view, illustrating a modified embodiment.

Firstly, an overview of a heating implement 1 will be described in reference to FIG. 1 to FIG. 3. FIG. 1 is a plan view from a side of a first sheet 11 of the heating implement 1, and FIGS. 2 and 3 are cross-sectional views along line II-II of FIG. 1. In this regard, a release paper 2 is attached to the heating implement 1 in FIGS. 2 and 3. The heating implement 1 of the present embodiment includes a first sheet 11 having air-permeability and being in contact with the body of the wearer and a second sheet 12 located in the other side than the side of a body of a wearer; a heating element 13 that produces steam when it generates heat, intermediately arranged between the first sheet 11 and the second sheet 12; and a first adhesive layer 14 and a second adhesive layer 15 provided in one of external surfaces of the first sheet 11 which is applied to the wearer side. Further, the heating implement 1 includes a region without adhesive layer, in which none of the first adhesive layer 14 and the second adhesive layer 15 is disposed, in at least a part of an external circumference section of the aforementioned first sheet 11. In such case, as shown in FIGS. 2 and 3, an inner bag 17 is provided with a sheet 171 having air-permeability and serving as a third sheet placed in the side of the first sheet 11 and a sheet 172 serving as a fourth sheet placed in the side of the second sheet 12 and the heating element 13 may be intermediately arranged in such inner bag 17. In such case, the sheet 171 is located in the side of the body of the wearer.

This heating implement 1 is configured so that the first sheet 11 is located in the side of the wearer when the heating implement 1 is put thereon. The term body of the wearer used in the present embodiment means any section, to which the heating implement 1 can be attached by the adhesive agent, and except the head such as the face. This includes, for example, the dorsal side, and more specifically the back side of the neck, a section from the back side of the neck to the shoulder, the back, the abdomens and the like.

The first adhesive layer 14 and the second adhesive layer 15 are provided on an external surface of the first sheet 11. These adhesive layers serve as fixing the heating implement 1 onto the skin of the wearer.

The first adhesive layer 14 is configured of a pair of first adhesive layers, which parallelly elongate in a single direction and are spaced apart from each other, and the second adhesive layer 15 is disposed in a region between a pair of the aforementioned first adhesive layers 14, and elongate in the same direction following the first adhesive layers 14.

In the plan view of the heating implement 1 from the side of the first sheet 11, the heating element 13 is located in a region between the first adhesive layer 14 and the second adhesive layer 15.

In the plan view of the heating implement 1 from the side of the first sheet 11, no adhesive layer is present in the region between the first adhesive layer 14 and the second adhesive layer 15, and an external surface of the first sheet 11 is configured so that air is supplied to the heating element 13.

The adhesive layer is preferably provided in a region that does not overlap with the heating element 13 in a plan view of the heating implement 1 from the side of the first sheet 11, and further, in view of ensuring the supply of air to the heating element 13, a region without adhesive layer is provided in at least a portion of the external circumference section of the first sheet 11. The external circumference section of the first sheet 11 is a vicinity of the circumference in the surface in contact with the wearer side of the first sheet 11, and is also the region outer than the circumference of the heating element 13. The size, the number and the position of the region without the adhesive layer are not particularly limited, and in view ensuring sufficient supply of air to the heating element 13, the region without the adhesive layer is preferably provided in a part of or all of the section between a pair of the first adhesive layers 14 provided spaced apart from each other, and is preferably provided in a part of or all of the section between the first adhesive layer 14 and the second adhesive layer 15 when the second adhesive layer 15 is provided. More specifically, in FIGS. 2 and 3, the first adhesive layer 14 and/or the second adhesive layer 15 may be divided into upper and lower sections, or may be arranged above and/or under the heating element 13, and a combination of the above-described division and the arrangement may be employed. For example, in the heating implement 1 in FIG. 1, three regions without the adhesive layer are provided above and under the circumference section of the first sheet 11, respectively.

Also, the heating implement 1 includes the second sheet 12 serving as an air-impermeable layer located in the opposite side to the first sheet 11 across the heating element 13. In addition to above, when the inner bag 17 is further provided and the heating element 13 is intermediately disposed in the inner bag 17 as shown in FIGS. 2 and 3, it is preferable to configure that the second sheet 12 is an air-permeable sheet and a sheet 172 constituting the inner bag 17 is impermeable. Hereinafter, the configuration provided with the inner bag 17 as shown in FIGS. 2 and 3 will be exemplarily described in the present invention.

Since the above-described heating implement 1 is configured that the air-impermeable sheet 172 is provided in the opposite side to the sheet 171 of the heating unit 18 containing the heating element 13 therein so that air is supplied to heating element through the air-permeable first sheet 11 and the sheet 171, water vapor generated in the heating element 13 is difficult to be released from the side of the second sheet 12 to the outside and thus water vapor generated in the heating element 13 can be preferentially released from the side of the first sheet 11. This allows definitely supplying water vapor to the skin of the wearer.

Also, in the plan view of the heating implement 1 from the side of the first sheet 11, no adhesive layer is present in a region between the first adhesive layer 14 and the second adhesive layer 15 and the external surface of the first sheet 11 is configured to cause the supply of air to the heating element 13 through the sheet 171. Thus, when the heating implement 1 is put thereon, a path elongating in a single direction that allows supplying air is created between the skin of the wearer and the first sheet 11, and thus air can be successfully supplied to the heating element 13 through the first sheet 11 and the sheet 171. This allows providing desired heat generation characteristics. In addition, when the heating implement 1 is adhered on the back side of the neck of the wearer, unwanted adhesion of hair or the like onto the adhesive layer of the heating implement 1 can be avoided.

Next, the heating implement 1 of the present embodiment will be described in detail in reference to FIGS. 1 to 8.

The first sheet 11 and the second sheet 12 constitute the outer sheath of the heating implement 1. In the present embodiment, the first sheet 11 and the second sheet 12 have the same dimension and the same two-dimensional geometry. In the present embodiment, the first sheet 11 and the second sheet 12, namely the heating implement 1 have horizontally long shape having longitudinal direction X and width direction Y perpendicular thereto in the plan view from the side of the first sheet 11. More specifically, the length in the X-axis direction is longer than the length of the Y-axis direction, and for example, the first sheet 11 and the second sheet 12 preferably have a horizontally long shape having the long side in the longitudinal direction: X direction; and the short side in the transverse direction: Y direction, and more specifically it is preferable to have the shape in the plan view of rectangular shape, ellipse shape, oval shape, beans shape, and the like.

As described above, the heating implement 1 is configured to have horizontally long flat shape in the plan view from the side of the first sheet 11, so that the heating implement 1 can be adhered on the dorsal section, more specifically, on the back side of the neck, the back, and the lumbar part, so as to elongate along the transverse direction of the wearer.

An outer bag (first accommodation body) housing the heating unit 18 in the interior thereof is configured in the heating implement 1 by bonding or by hermetically sealing the circumferences of the first sheet 11 and the second sheet 12 together.

In addition to above, as previously described, the first sheet 11 and the second sheet 12 may be composed of separate sheets and the associated circumferences thereof may be bonded together or by hermetically sealed to configure the bag, or alternatively, the first sheet 11 and the second sheet 12 may be composed of a continuous sheet, and such continuous sheet may be folded and the opposing circumferences may be bonded together or hermetic sealed to configure the bag.

When the wearer puts on the heating implement 1, the first sheet 11 is located in the side of the skin of the wearer. The first sheet 11 is an air-permeable sheet, and the lower limit of the air resistance is not particularly limited and may be even 0 second/100 ml, and in consideration of the prevention of the see-through appearance of the inner bag 17 located in the inside thereof and the grammage required for obtaining the sufficient strength to maintain the form of the sheet, the air resistance is preferably equal to or higher than 1 second/ 100 ml. On the other hand, the air resistance of the first sheet 11 is preferably equal to or lower than 1,000 second/100 ml in terms of not obstructing the air-permeability of the sheet 171, and is more preferably equal to or lower than 100 second/100 ml, and is further preferably equal to or lower than 10 second/100 ml.

Fiber sheets including nonwoven fabrics and the like may be employed for the first sheet 11.

The air resistance is a value measured according to JIS P 8117 (1998), and is defined as time required for air of 100 ml passing through an area of 6.45 cm$^2$ under the constant pressure. Consequently, larger value of the air resistance means taking longer time for air passage, and thus indicates lower air-permeability. Conversely, lower air resistance indicates higher air-permeability. As described above, the level of air resistance and the level of air-permeability are in inverse relation. The air resistance can be determined with OKEN-type air-permeability and smoothness tester.

The second sheet 12 is configured of an air-permeable sheet, similarly as in the first sheet 11 in the present embodiment. However, from the viewpoint of the aesthetic appearance, it is preferable to be configured of a nonwoven fabric, similarly as in the first sheet 11.

Meanwhile, the heating implement 1 may be configured to be stretchable in at least X-axis direction. For example, the first sheet 11 and the second sheet 12 may be configured of stretchable sheets, which have air-permeability as described above and are stretchable in X-axis direction. Typical stretchable sheet includes, for example, synthetic fibers selected from polyesters such as PET (polyethylene terephthalate) and the like, polyolefins such as PE (polyethylene), PP (polypropylene) and the like, polyamides, polyacrylics and the like; natural fibers selected from cellulose, silk, cotton, wool and the like; or sheets constituted of the complex fibers obtained by combining these fibers. On the other hand, for the stretchable sheet nonwoven fabric can be used. Alternatively, nonwoven fabrics produced by employing two or more types of fibers via a process selected from: air-through process, spunbonding process, needle punching process, meltblown process, carding process, thermal bonding process, spunlace process, and solvent-bonding process may also be used for the stretchable sheet. Further, a knitting cloth may also be used, as well as the nonwoven fabrics. In view of the texture or the elasticity, it is more preferable to use the nonwoven fabric having stretching properties as the stretchable sheet. The air-through nonwoven fabrics and the spunbonded nonwoven fabrics having elastic fibers (for example, polyurethane, polyester) as the constitution fiber and the like are preferable for the nonwoven fabrics having stretching properties, and the nonwoven fabric, which is surface-treated with silicone or a surface-active agents may also be used in view of the texture. In addition to above, the first sheet 11 and the second sheet 12 may be the stretchable sheets configured of the same materials, or may be the stretchable sheets configured of the different materials.

The heating element 13 is housed in the inner bag 17, and is disposed between the first sheet 11 and the second sheet 12, serving as the heating unit 18. This heating element 13 functions as generating vapor when it generates heat, and is composed of an oxidizeable metal, water, an exothermic composition containing a carbon component.

The oxidizeable metal is a metal generating oxidizing reaction heat, and is typically the powder or the fiber of, for example, iron, aluminum, zinc, manganese, magnesium, calcium, a mixed metal of two or more of these metals, and the like, and iron is preferable in view of the cost, the versatility and the easiness in the handling.

The carbon component typically the component having water retention capability, oxygen supply ability, and catalytic ability, and one, two or more selected from, for example, activated carbon, acetylene black, and graphite can be used, and activated carbon is preferable in view of providing reduced cost and increased exothermic efficiency.

The content of the carbon component in the heating implement 1 is obtained as the amount of carbon over the entire area of the heating implement 1 in plan view. The entire area of the heating implement 1 in plan view is equivalent to the area of the surface of the heating implement 1 attached on the body, and in the present embodiment, it is the area of the most outer surface, namely the first sheet 11 disposed on the body side, of the heating implement 1. However, the surface attached on the body is not limited to the section having the adhesive layer formed thereon. In addition, sections attached to the heating implement 1, or namely sections that are not directly relevant to the effect of the heating implement 1, such as for example, a tongue section provided for easily removing the heating implement 1 after the use, are not included in the entire area of the heating implement 1 in plan view.

The content of the carbon component in the heating implement 1 is preferably equal to or larger than 0.89 mg/cm$^2$ in view of the heat generation characteristics, and is more preferably equal to or larger than 0.96 mg/cm$^2$, and is further preferably equal to or larger than 1.04 mg/cm$^2$, and on the other hand, is preferably equal to or smaller than 1.63 mg/cm$^2$ in view of exhibiting the volatilization effect of the fragrance, and is more preferably equal to or smaller than 1.38 mg/cm$^2$, and is further preferably equal to or smaller than 1.26 mg/cm$^2$. Also, it is preferably 0.89 to 1.63 mg/cm$^2$, and is more preferably 0.96 to 1.38 mg/cm$^2$, and is further preferably 1.04 to 1.26 mg/cm$^2$. This allows exhibiting the volatilization effect of the fragrance, while inhibiting the deterioration of the adhesive force and the heat generation characteristics due to the adsorption of the fragrance by the adhesive agent and the carbon component.

The content of the carbon component in the heating implement 1 can be determined by, for example, the following manner.
(1) Around 3 g of the heating element is weighted within nitrogen gas stream, and then is dried at 120 degrees C. for 30 minutes, and the water content is measured.
(2) The dry matter obtained in the aforementioned (1) is dispersed in a small amount of water (3 ml) to prepare a slurry-like product.
(3) 75% aqueous solution of sodium metatungstate is prepared, and the carbon component and the oxidizeable metal are separated by the density gradient centrifugation process. Mass ratio of slurry-like product: sodium metatungstate aqueous solution is adjusted to fall within the range of from 3:25 to 5:25, and a centrifugal separation process is conducted at 5 degrees C. and 10,000 rounds for 30 minutes.
(4) The slurry in the upper portion containing the carbon component is recovered, and the recovered product is rinsed with water for several times to remove salts and water-soluble inorganic matters, and then the dried mass thereof is measured, which is divided by the total area in plan view of the heating implement 1 to calculate the content of the carbon component.

The heating element 13 may be powder or formed product of powder, or may be sheet-like product, and in the present embodiment, is a sheet-like product of rectangular shape (square, rectangle) in plan view.

The heating element 13 may be a product obtained according to a process, in which, for example, a slurry-like product containing the exothermic composition stated above is produced, and this slurry-like product is applied over a base material layer S (see FIG. 2) or over a base material layer R (see FIG. 10) as will be discussed later.

In such case, the heating element 13 will be housed in the inner bag 17 as will be discussed later, together with the base material layer R and the base material layer S.

The base material layer S preferably serves as absorbing and retaining water and employs a sheet being air-permeable. The base material layer S may absorb a certain amount of water in the exothermic composition. The air resistance of the base material layer S (condition of absorbing water) is preferably equal to or lower than 5,000 second/100 ml, and is further preferably equal to or lower than 1,000 second/100 ml. And on the other hand, although the lower limit is not particularly limited, it is preferably equal to or higher than 0 second/100 ml, and is further preferably equal to or higher than 1 second/100 ml.

Typical base material layer S includes, for example, fiber sheets of materials made of fiber as its raw material, such as paper, nonwoven fabric, cloth, knitted web and the like. The above-described fibers typically includes, for example, fibers composed of natural fibers such as plant fibers and animal fibers as the main constituent, or composed of chemical fibers as the main constituent. In addition, in order to facilitate the absorption and retention of water, water-absorbing material such as for example gelatinized starch and water absorbent polymer and the like may be contained as required.

In addition to above, when the wearer put on the heating implement 1 on the skin, the base material layer S may be positioned in the side that is closer to the skin than the heating element 13, or may be positioned in the side that is further from the skin than the heating element 13.

Figure 10:
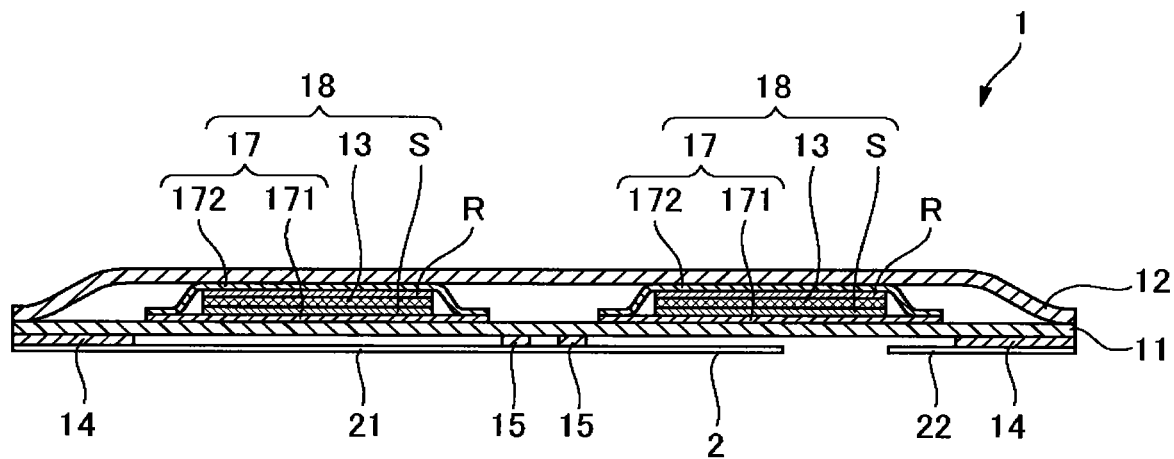
FIG. 10 is a cross-sectional view, illustrating a modified embodiment of a heating implement.

When the heating element 13 is in powder-like condition or slurry-like condition, the heating element 13 may be in the form of the ternary-layered structure including base material layers S and R (from the side of the sheet 172: base material layer R/heating element 13/base material layer S), in order to facilitate the housing thereof in the inner bag 17 (FIG. 10). In consideration of the operability for housing thereof in the inner bag 17, the grammage of the base material layer R may be equal to or smaller than 80 g/m$^2$, and is preferably equal to or smaller than 50 g/m$^2$, and is more preferably equal to or smaller than 35 g/m$^2$, and on the other hand is preferably equal to or larger than 15 g/m$^2$ in view of film-formability. The base material layer R may be either air-permeable or air-impermeable, and in the case of being air-permeable, the air resistance is preferably equal to or lower than 5,000 second/100 ml, and is more preferably equal to or lower than 1,000 second/100 ml. On the other hand, although the lower limit is not particularly limited, it is preferably equal to or higher than 0 second/100 ml, and is more preferably equal to or higher than 1 second/100 ml. For example, polyethylene (PE) or polypropylene (PP) etc. are used for the material of the base material layer R.

In addition, the heating element 13 may be a product manufactured by a paper-making process using a paper-making machine. In this case, the exothermic composition preferably contains a fiber material, in addition to the above-described respective components. In this case, the base material layer S may be omitted as shown in FIG. 3.

Figure 4:
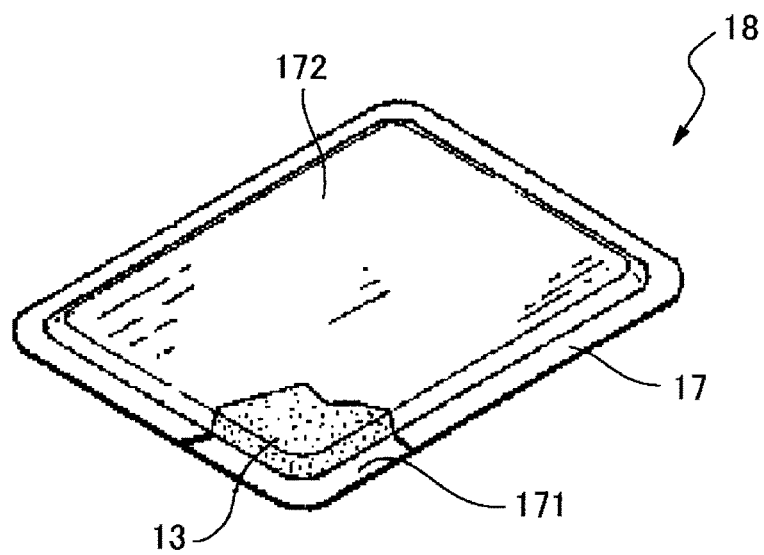
FIG. 4 is a perspective view, illustrating a heating unit.

The above-described heating element 13 is, as shown in FIGS. 2 to 4, housed in the inner bag (second accommodation body) 17. The heating unit 18 is configured of the heating element 13 and the inner bag 17.

The circumference sections of the sheet 171 and the sheet 172 are joined together to configure the inner bag 17. The region of the sheets 171 and 172 except the circumference sections is a non-joining region, and the heating element 13 is disposed in the non-joining region.

The sheet 171 is positioned in the side that is closer to the skin than the heating element 13 when the wearer put on the heating implement 1 on the skin.

The sheet 171 is a sheet constituting the heating unit 18, and is air-permeable. The air resistance of the sheet 171 is preferably equal to or higher than 500 second/100 ml, in view of suitably controlling the exothermic temperature and preventing abnormal heat generation, and is more preferably equal to or higher than 800 second/100 ml, and is further preferably equal to or higher than 1300 second/100 ml. On the other hand, in view of obtaining improved temperature rising (within 5 minutes), it is preferably equal to or lower than 5000 second/100 ml, and is more preferably equal to or lower than 3500 second/100 ml. As the sheet 171 having the above-described air resistance, it is preferable to use a porous sheet made of a synthetic resin, which, for example, has moisture-permeability but has no water-permeability. More specifically, a film made by stretching polyethylene containing calcium carbonate can be used. In addition to above, if no inner bag 17 is provided as described above, it is preferable to provide to the first sheet 11 the equivalent level of the air resistance as that of the sheet 171.

The sheet 172 is positioned in the side that is further from the skin than the heating element 13 when the wearer put on the heating implement 1 on the skin.

The sheet 172 is, in the present embodiment, an air-impermeable sheet having substantially no air-permeability. Here, the air-impermeable sheet having substantially no air-permeability is a conception including not only the air-impermeable sheet that completely shields air, but also a sheet having poor air-permeability, which does not affect the heat generation characteristics of the heating element 13 even if air might be passed through the sheet (more specifically, providing the heat generation characteristic that is equivalent to those obtained by using the air-impermeable sheet that completely shields air). The air resistance of the air-impermeable sheet is equal to or higher than 80,000 second/100 ml, and is preferably equal to or higher than 100,000 second/100 ml. It is further preferably equal to or higher than 150,000 second/100 ml.

A film made of a synthetic resin, such as a single-layered or multiple-layered polyethylene film and the like can be used for the sheet 172. In addition, a product made by laminating various types of fiber sheets including one, two or more of nonwoven fabric(s) selected from needle punched nonwoven fabric, air through nonwoven fabric and spunbonded nonwoven fabric and a paper obtained by paper-making process over the outer surface of the single-layered or multiple-layered film of the synthetic resin, can be used. The above-described fiber sheets and papers are preferable, since these forms the most outer surface of the sheet 172 so that the sheet 172 is configured to contain the fiber sheet and the paper, resulting in easier retention of the perfuming fragrance. In addition to above, if no inner bag 17 is provided as described above, it is preferable that the second sheet 12 is the air-impermeable sheet having substantially no air-permeability, similarly as the sheet 172.

Here, since the heating implement 1 has the air-impermeable sheet 172, the air-permeability of the whole sheet layer configured of the second sheet 12, the sheet 172 and the base material layer R (except base material layer R when no base material layer R is used) is lower than the air-permeability of the whole sheet layer configured of the first sheet 11, the sheet 171 and the base material layer S (except base material layer S when no base material layer S is used). In other words, the air resistance of the whole sheet layer from the second sheet 12 to the heating element 13, which has the second sheet 12 as the outermost layer, is higher than the air resistance of the whole sheet layer from the first sheet 11 to the heating element 13, which has the first sheet 11 as the outermost layer.

The above-described heating unit 18 in the present embodiment has is the rectangular shape (more preferably square shape) in plan view.

The above-described heating unit 18, in turn, is housed in the inside of the outer bag configured of the above-described first sheet 11 and the second sheet 12. In the present embodiment, a plurality of heating units 18 are housed in the outer bag. A plurality of heating units 18 are arranged spaced apart from each other along the X-axis direction of the outer bag. One side of the heating unit 18 may be parallel with a longer side of the outer bag. A part of the sheet 172 of the heating unit 18 may be fixed to the second sheet 12 via an adhesive such as a hot melt-type adhesive.

In the present embodiment, an air-permeable layer for supplying air to the heating element 13 is formed by the first sheet 11, the sheet 171 and the base material layer S. In addition to above, when the heating element 13 is not formed on the base material layer S, the aforementioned air-permeable layer is configured of the first sheet 11 and the sheet 171.

Next, the first adhesive layer 14 and the second adhesive layer 15 will be described in reference to FIGS. 1 to 3.

The first adhesive layer 14 and the second adhesive layer 15 are provided on the outer surface of the first sheet 11. The first adhesive layer 14 and the second adhesive layer 15 serve for attaching the heating implement 1 to the skin of the wearer.

The first adhesive layer 14 consists of a pair of adhesive layers, and the pair of the first adhesive layers 14 elongate parallelly in a single direction and are arranged spaced apart from each other on the outer surface of the first sheet 11, and preferably are disposed in end sections of the first sheet 11 in X-axis direction, respectively. More preferably, the pair of the first adhesive layers 14 are arranged on both sides interposing the center line C passing through the center of the outer surface of the first sheet 11 in X-axis direction (vertical center line extending to transverse direction), and are preferably arranged in symmetric positions.

In the present embodiment, each of the first adhesive layers 14 elongates along the Y-axis direction of the first sheet 11 without intersecting with the second adhesive layer 15, and preferably, both ends in the elongating direction reach to the circumference of the first sheet 11. This allows stably adhere the heating implement 1 to the wearer, and further, when the heating implement 1 is put on, a path elongating in a single direction for allowing air to be supplied between the skin of the wearer and the first sheet is created, so that air can be successfully supplied to the heating element through the first sheet 11.

More preferably, the pair of the first adhesive layers 14 are formed so that the circular arc-shaped circumference overlaps with the circumference in Y-axis direction (circular arc part) of the first sheet 11, in plan view from the side of the outer surface of the first sheet 11, and thus are semicircle-shaped.

In FIG. 1, in plan view from the side of the first sheet 11, the first adhesive layer 14 and the second adhesive layer 15 are provided in the region of the first sheet 11 where none of the heating unit 18 is located.

In addition to above, it is preferable in terms of the heat generation characteristics that the pair of the first adhesive layers 14 do not overlap with the heating element 13 in plan view from the side of the outer surface of the first sheet 11.

On the other hand, in plan view from the side of the first sheet 11, the second adhesive layer 15 is arranged in the region of between the pair of the first adhesive layers 14 and elongates in the same direction following the first adhesive layers 14. The second adhesive layer 15 elongates along the same direction as the pair of the first adhesive layers 14 elongate, or in other words along the Y-axis direction of the first sheet 11. This allows stably adhere the heating implement 1 to the wearer, and further, when the heating implement 1 is put on, a path elongating in a single direction for allowing air to be supplied between the skin of the wearer and the first sheet 11 is created, so that air can be successfully supplied to the heating element 13 through the first sheet 11.

In the present embodiment, the second adhesive layer 15 is in rectangular shape in plan view from the side of the first sheet 11. Then, the both ends in the elongating direction of the second adhesive layer 15 preferably reach to the circumference of the first sheet 11. More specifically, the second adhesive layer 15 is preferably formed so as to cover the overall length of the first sheet 11 in the Y-axis direction.

In addition, the first adhesive layers 14 are disposed in the end sections of the heating implement 1 in the X-axis direction and the second adhesive layer 15 is provided in vicinity of the center line C, such that the region between the first adhesive layer 14 and the second adhesive layer 15 is ensured to be broad, in plan view from the side of the first sheet 11 where the heating element 13 is located, and therefore, when the heating implement 1 is put on, a path elongating in a single direction for allowing air to be supplied between the skin of the wearer and the first sheet 11 is created, so that air can be successfully supplied to the heating element 13 through the first sheet 11, and further, the configuration is preferable since the heating implement 1 can be definitely fixed to the wearer. For example, even if the heating implement 1 is adhered to a body section that is capable of unusually moving, such as the neck or the dorsal section from the neck to the shoulder of the wearer, such configuration can prevent unwanted removal of the heating implement 1.

Figure 9:
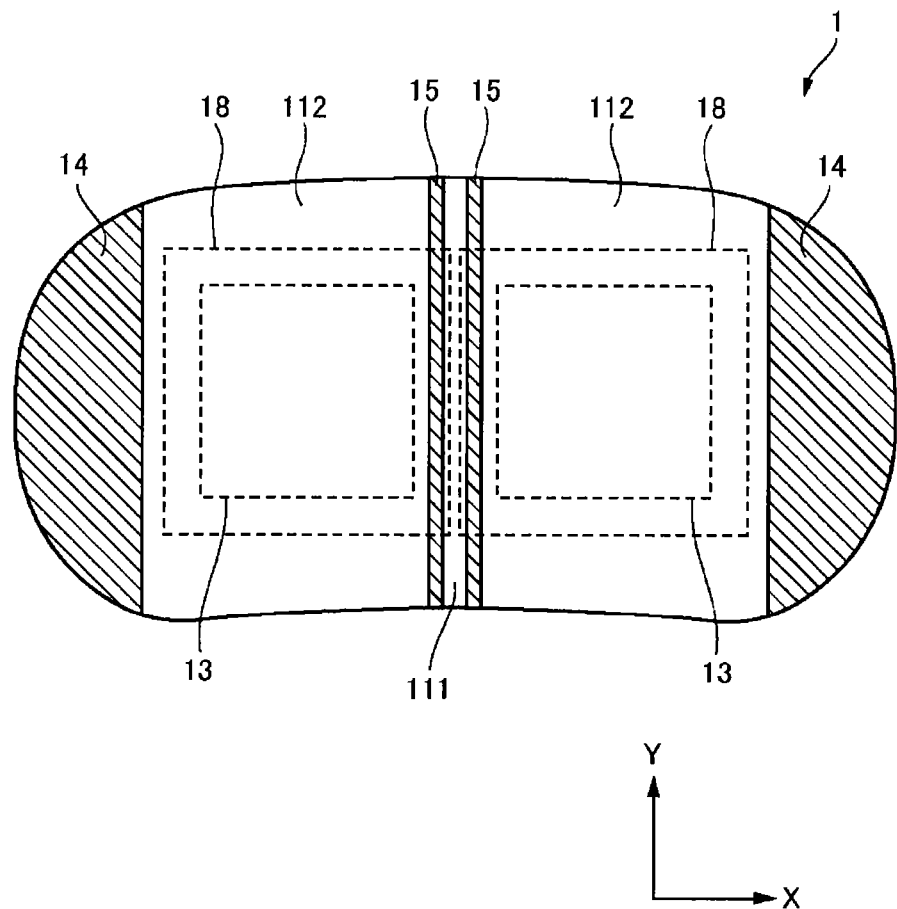
FIG. 9 is a plan view, illustrating a modified embodiment of a heating implement.
Figure 12:
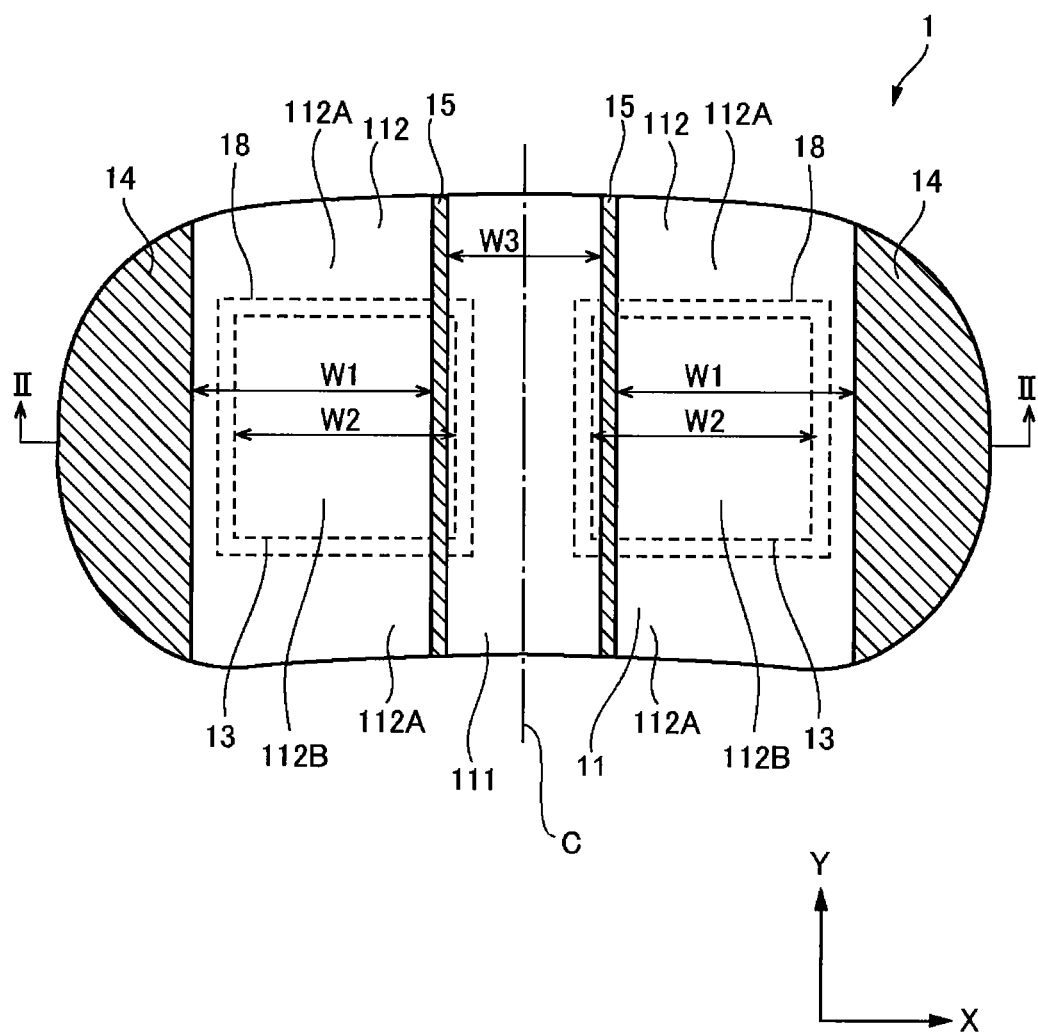
FIG. 12 is a plan view, illustrating a modified embodiment of a heating implement.

While the exemplary implementation of providing the second adhesive layer 15 in the position in vicinity of the center line C has been described above, the position of the second adhesive layer 15 is not limited thereto. For example, this may move in parallel in the longitudinal direction from the center line C. More specifically, in plan view of the heating implement 1 from the side of the first sheet 11, the second adhesive layer 15 may not overlap with the heating element 13 but may overlap with the heating unit 18 as shown in FIG. 9 in view of the heat generation characteristics, and further, as shown in FIG. 12, it may be arranged that the second adhesive layer 15 partially overlaps with the heating element 13, in view of the adhesive force.

In the present embodiment, a plurality of second adhesive layers 15 are provided, and each of the plurality of second adhesive layers 15 are spaced apart from each other. In the present embodiment, two second adhesive layers 15 are provided. A plurality of second adhesive layers 15 are preferably arranged in symmetric positions across the center line C. A plurality of second adhesive layers 15 preferably elongate along the Y-axis direction of the first sheet 11. In the present embodiment, the pair of the second adhesive layers 15 elongate in parallel.

In the present embodiment, an exposed region 111 (region without adhesive layer), in which none of the adhesive layer is present and thus the outer surface of the first sheet 11 is exposed, is formed between the pair of the second adhesive layers 15, and the exposed region 111 elongates in the Y-axis direction, and is in rectangular shape in plan view. The both ends in the Y-axis direction of the exposed region 111, which is the region without adhesive layer, preferably reach to the circumference of the first sheet 11. In the present embodiment, this exposed region 111 is located in the center in the X-axis direction of the first sheet 11, and the above-described center line C passes through the inside of the exposed region 111. As will be specifically discussed later, such center line C serves as the folding line for the heating implement 1. None of the adhesive layer is preferably present on this folding line.

In addition to above, in the present embodiment, it is preferable to avoid the exposed region 111 from being overlapped with the heating element 13 and further with the heating unit 18 in plan view from the side of the first sheet 11, in view of the easiness for folding and the fitting-capability to the body. However, as shown in FIG. 9, the exposed region 111 may overlap with the heating unit 18.

As shown in FIG. 1, exposed regions 112 (regions without adhesive layer), in which none of the adhesive layer is present and thus the outer surface of the first sheet 11 is exposed, are formed in the regions between the first adhesive layers 14 and the second adhesive layers 15 adjacent to the outer surface of the first sheet 11. In the present embodiment, a pair of exposed regions 112 are formed in outer surface of the first sheet 11.

While the shape and the size of the pair of exposed regions 112 are the same in the present embodiment, these may alternatively be different. Here, the exposed region 112 is a region enclosed by one side in the side of the heating element 13 of the first adhesive layer 14, one side in the side of the heating element 13 of the second adhesive layer 15, and the circumference of the first sheet 11. As described above, none of the adhesive layer is present in the region between the first adhesive layer 14 in the outer surface of the first sheet 11 and the adjacent second adhesive layer 15, such that disturbance in the flow of air due to the adhesive layer is reduced, and air can be successfully passed between the skin of the wearer and the heating element 13 through exposed region 112.

The exposed region 112 includes a pair of the exposed regions, namely an exposed region (first exposed region) 112A, and an exposed region (second exposed region) 112B. The exposed region 112A is a region located outer in Y-axis direction than the heating element 13.

The exposed region 112A sandwiches the heating element 13 in a direction that is different from direction (orthogonal direction in the present embodiment) in which the first adhesive layer 14 and the second adhesive layer 15 sandwich the heating element 13, and extends from the circumference of the heating element 13 (in FIG. 1, upper side or lower side separating the heating element 13) and reaches to the circumference of the first sheet 11. The exposed region 112A is a section that serves a critical role in the air supply to the heating element 13.

The exposed region 112A can be formed to have larger area by presenting the exposed region 112A as an entire region enclosed with an extension line extending along the X-axis direction the side of the heating element 13 in the X-axis direction, one side of the first adhesive layer 14 in the side of the heating element 13, one side of the second adhesive layer 15 in the side of the heating element 13 and the circumference of the first sheet 11, without any adhesive layer interposed between the circumference of the heating element 13 and the circumference of the first sheet 11.

Air is successfully supplied to the heating element 13 by forming the exposed region 112A. In addition, the formation of the exposed region 112A allow that, when the heating implement 1 is adhered on the back side of the neck or the side of the back of the wearer, unwanted adhesion of hair or the like onto the adhesive layer of the heating implement 1 can be avoided. This allows providing the heating implement 1 with excellent handle-ability.

The exposed region 112B is provided adjacent to the exposed region 112A and continually with the exposed region 112A. This exposed region 112B covers the heating element 13, and serves as another section that plays a critical role in supplying air to the heating element 13. In the present embodiment, the whole heating element 13 is covered with the exposed region 112B in plan view taking from the external side of the first sheet 11. In other words, the first adhesive layer 14 and the second adhesive layer 15 are disposed so as not to overlap with the heating element 13, and thus the heating element 13 is not covered with the adhesive layer. Such configuration allows easily supplying air to the heating element 13. In addition, vapor generated from the heating element 13 can be definitely supplied to the wearer. As described above, the exposed region 112A is formed to have larger area. This allows definitely supplying air to the exposed region 112B disposed adjacent to the exposed region 112A, and thus air can be sufficiently supplied to the side of the heating element 13 through the exposed region 112B.

In the present embodiment, the width W1 of the exposed region 112 in the X-axis direction is longer than the width W2 of the heating element 13 in the X-axis direction, and further, is longer than the width of the heating unit 18 in the X-axis direction, and the length of the exposed region 112 in the Y-axis direction is longer than the length of the heating element 13 in the Y-axis direction, and further, than the length of the heating unit 18 in the Y-axis direction.

In addition to above, while the width W1 of the exposed region 112 in the X-axis direction is longer than the width W2 of the heating element 13 in the X-axis direction, this may be shorter than the width of the heating unit 18 in the X-axis direction (see FIG. 9).

In addition, the width W1 of the exposed region 112 in the X-axis direction is larger than the width W3 of the exposed region 111 in the X-axis direction, and for example, the width W1 is 3 folds to 15 folds of the width W3.

In addition to above, the first adhesive layer 14 and the second adhesive layer 15 are formed by applying an adhesive agent containing at least one, two or more selected from acrylic-based resins, vinyl acetate-based resins, olefin-based resins and rubber-based resins to the outer surface of the first sheet 11. Among these, it is preferable to use at least one, two or more selected from vinyl acetate-based resins, olefin-based resins and rubber-based resins for the resins for forming the adhesive layer, since these allows preparing a hot melt adhesive agent.

It is preferable to use the hot melt adhesive agent as the adhesive agent for the first adhesive layer 14 and the second adhesive layer 15, in view of its higher cohesive force. The hot melt adhesive agent generally contains an adhesive basis, a tackifying resin and a softening agent as the constituent components.

Typical adhesive basis includes styrene-butadiene rubber (SBR), styrene-butadiene-styrene block copolymer (SBS), styrene-isoprene-styrene block copolymer (SIS), styrene-ethylene-butylene-styrene block copolymer (SEBS), styrene-ethylene-propylene-styrene block copolymer (SEPS) and the like. The blending amount of the adhesive basis is preferably from 5 to 50% by weight, and is more preferably configured to be from 10 to 40% by weight.

Typical tackifying resin includes rosin and rosin derivative, terpene resins and petroleum resins, and typical petroleum resins includes aliphatic-based petroleum resins, aromatic-based petroleum resins, dicyclopentadiene-based petroleum resins, copolymers thereof and hydrogenated petroleum resins. The blending amount of the tackifying resin is preferably from 10 to 60% by weight, and is more preferably configured to be from 20 to 50% by weight.

Typical softening agent component includes processing oils, mineral oils, various types of plasticizers, polybutene and liquid tackifying resins and the like, which have the softening point of equal to or lower than 10 degrees C. and the weight average molecular weight of from 200 to 700. The blending amount of the softening agent component to the whole adhesive agent is preferably from 10 to 60% by weight, and is more preferably configured to be from 20 to 50% by weight.

In addition to the above-described components, known additives such as an antioxidant or an ultraviolet absorber and the like may be suitably blended in the hot melt adhesive agent. For example, phenolic-based antioxidant, amine-based antioxidant, phosphorus-based antioxidant and benzimidazole-based antioxidant are employed for the antioxidant.

The amount of the coating of the above-described hot melt adhesive agent is preferably from 140 to 220 g/m$^2$, and is more preferably from 150 to 200 g/m$^2$ in view of the presentation of sufficient adhesive force and the prevention of the adhesive agent from remaining on the skin.

Figure 5:
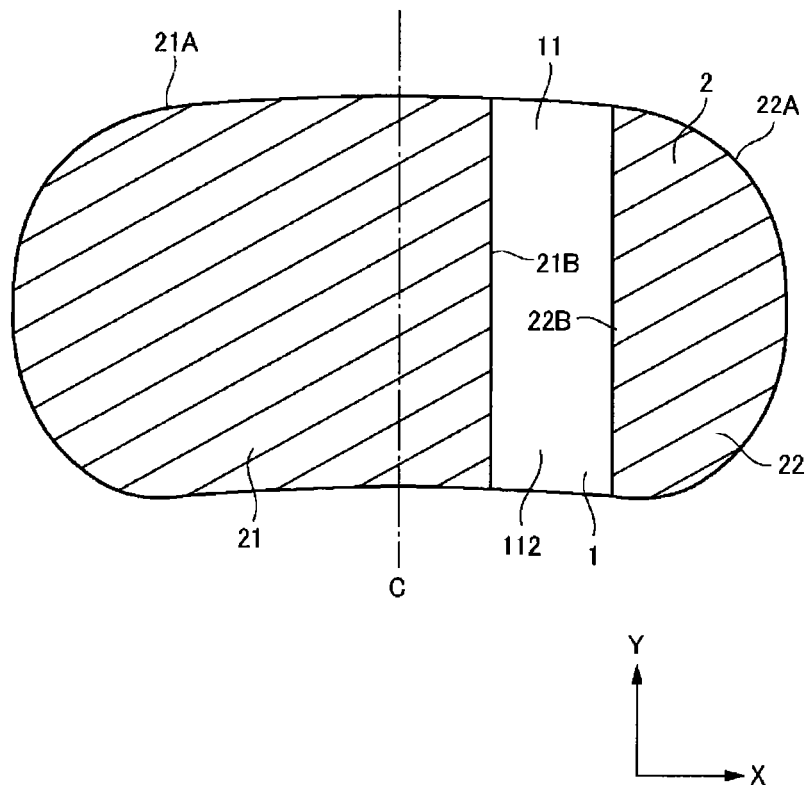
FIG. 5 is a plan view, illustrating a state, in which a release paper is provided to a heating implement.

Next, the release paper 2 will be described in reference to FIGS. 2, 3 and 5. FIG. 5 is a plan view, illustrating a condition, in which the release paper 2 is put on the heating implement 1 of FIG. 1.

The release paper 2 is provided in the heating implement 1 so as to cover the entire area of the adhesive layer.

The release paper 2, is preferably configured of at least one pair of releasing sections 21 and 22, and in the present embodiment is configured of a pair of the releasing sections 21 and 22.

In the present embodiment, the releasing section 21 partially covers one first adhesive layer 14 of the pair of the first adhesive layers 14, one of exposed regions 112, one second adhesive layer 15 of the pair of the second adhesive layers 15, the exposed region 111, the other second adhesive layer 15 of the pair of the second adhesive layers 15 and the other the exposed region 112. And, the releasing section 21 adheres to one first adhesive layer 14 of the pair of the first adhesive layers 14 and both of the pair of the second adhesive layers 15.

As shown in FIG. 5, the circumference of the releasing section 21 is configured of a circumference section 21A overlapping with the circumference of the first sheet 11 and a circumference section 21B elongating over the other exposed region 112 in the Y-axis direction.

In the present embodiment, the releasing section 22 partially covers the other first adhesive layer 14 of the pair of the first adhesive layers 14 and the other of the exposed regions 112. The releasing section 22, in turn, adheres to the other first other adhesive layer 14 of the pair of the first adhesive layer 14.

As shown in FIG. 5, the circumference of the releasing section 22 is composed of a circumference section 22A overlapping with the circumference of the first sheet 11 and a circumference section 22B elongating on the other of the exposed regions 112 in the Y-axis direction.

As described above, in plan view from the side of the first sheet 11, the geometry of the releasing section 21 is different from the geometry of the releasing section 22. In addition, in plan view from the side of the first sheet 11, the releasing section 21 is located spaced apart from the releasing section 22, and the circumference section 21B faces to the circumference section 22B. In addition, the circumference section 22B and the circumference section 21B are positioned on the other of the exposed regions 112, and the outer surface of the first sheet 11 is exposed from the space between the circumference section 22B and the circumference section 21B. In the present embodiment, the other of the exposed regions 112 is exposed. The circumference section 21B and the circumference section 22B is positioned offset from the center line C in the X-axis direction.

As described above, the circumference section 21B of the releasing section 21 and the circumference section 22B of the releasing section 22 are positioned on the exposed region 112. Thus, a region in vicinity of the circumference section 21B of the releasing section 21 and a region in vicinity of the circumference section 22B of the releasing section 22 are not adhered to the adhesive layer. This allows the wearer to easily pick up the region in vicinity of the circumference section 21B of the releasing section 21 and the region in vicinity of the circumference section 22B of the releasing section 22. Accordingly, the release paper 2 can be easily removed from the heating implement 1. In the present embodiment, the width W1 of the exposed region 112 in the X-axis direction is wider than the width W3 of the exposed region 111 in the X-axis direction. Thus, the configuration, in which the circumference sections 21B and 22B are disposed on the exposed region 112, is adopted to easily ensure wider distance between the circumference sections 21B and 22B and the adhesive layer, in comparison with the configuration, in which the circumference sections 21B and 22B of the releasing sections 21 and 22 are disposed on the exposed region 111. More specifically, this configuration allow ensuring wider distance between the circumference section 21B of the releasing section 21 and the second adhesive layer 15 and wider distance between the circumference section 22B of the releasing section 22 and the first adhesive layer 14, and ensuring wider region of the releasing section 21 that is not adhered to the adhesive layer in vicinity of the circumference section 21B and wider region of the releasing section 22 that is not adhered to the adhesive layer in vicinity of the circumference section 22B.

Further, the whole area of the release paper 2 can be reduced by broadening the distance between the circumference section 21B of the releasing section 21 and the circumference section 22B of the releasing section 22. Thus the amount of the garbage can be reduced and the cost can also be reduced.

Here, the size of the heating implement 1 will be described.

The heating implement 1 is put on the neck of the wearer, and is more specifically put on a section from the back side of the neck to the dorsal side, and the length thereof in the X-axis direction is, for example, from 10 to 30 cm, and the length in the Y-axis direction is from 5 to 10 cm.

In addition, the maximum width of the first adhesive layer 14 in the X-axis direction is from 10 to 80 mm, and the width of the second adhesive layer 15 in the X-axis direction is from 2 to 10 mm, and the maximum width W3 of the exposed region 111 in the X-axis direction is, for example, from 4 to 10 mm, and the width W1 of the exposed region 112 in the X-axis direction is, for example, from 15 to 130 mm.

Figure 6:
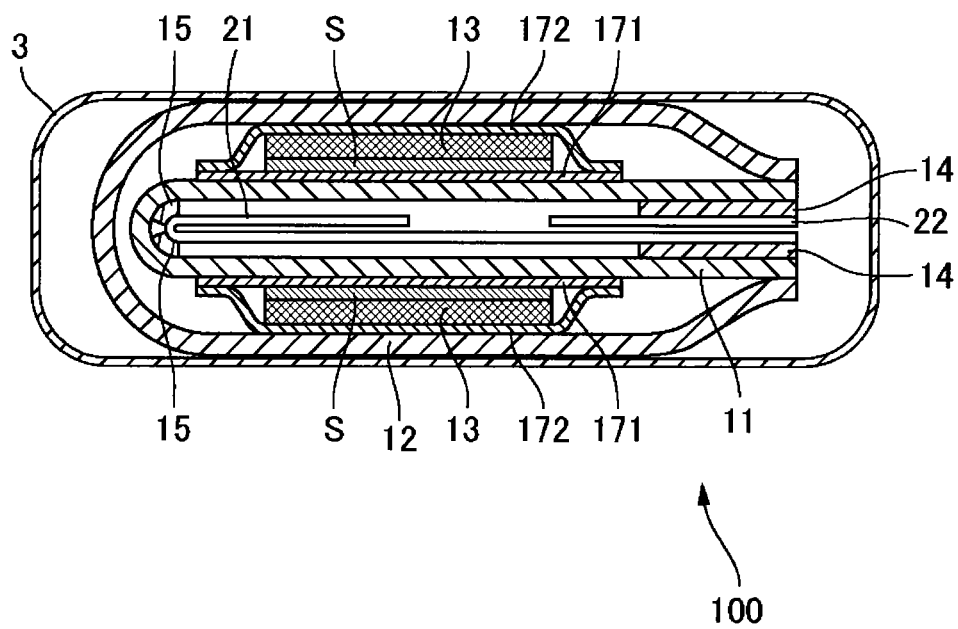
FIG. 6 is a cross-sectional view, illustrating a state, in which a heating implement is housed in an exterior package.

The above-described heating implement 1 is housed in the inside of an exterior package (packaging body) 3 in the condition that the release paper 2 is attached thereto, as shown in FIG. 6. This allows inhibiting the oxidation of the carbon component.

The heating implement 1 to which the release paper 2 is attached is folded into two sections. More specifically, the exposed region 111 is folded along the center line C in the elongating direction. In such case the heating implement 1, together with the release paper 2, are folded, so that the first adhesive layer 14 and the second adhesive layer 15 are located in the inside thereof.

Then, this is housed in the inside of the exterior package 3, and the exterior package 3 is sealed. The exterior package 3 is composed of a film having oxygen barrier property. The above-described exterior package 3 and the heating implement 1 to which the release paper 2 is attached can constitute the heat generation article 100.

Since the exposed region 111 without any adhesive layer is folded in the present embodiment, the heating implement 1 is easy to be folded. On the contrary, when the heating implement 1 to which the release paper 2 is attached is folded with the release paper 2 so that the adhesive layer is in the inside, the adhesive agents agglomerate to form clumping of the adhesive agents, since the release paper is extremely thinner than the body of the heating implement 1 and exhibit poor stretching property, and thus it may become difficult to extend the folded heating implement 1 upon the use of the heating implement 1.

On the contrary, since the exposed region 111 without containing the adhesive layer is folded in the present embodiment, the folded heating implement 1 can be easily extend.

Also, since the exposed region 111 does not overlap with the heating element 13 and it is not necessary to fold the heating element 13, the heating implement 1 can be smoothly folded and extended. Since the exposed region 111 has no overlapped portion not only with the heating element 13 but also with the heating unit 18 in the present embodiment, the heating implement 1 can be smoothly folded and extended.

Further, in the present embodiment, the heating implement 1 is fixed to the skin of the wearer by the first adhesive layer 14 and the second adhesive layer 15. Thus, it is considerably preferable that the heating implement 1 is folded with the release paper 2 so that the first adhesive layer 14 and the second adhesive layer 15 are in the inside, and is housed in the exterior package 3, such that the first adhesive layer 14, the second adhesive layer 15 and the first sheet 11 can be suitably protected.

Also, the heating implement 1 is folded to be housed in the inside of the exterior package 3, such that the heating implement 1 can be compactly housed in the inside of the exterior package 3 and the downsizing of the whole heat generation article 100 can be achieved.

Figure 7:
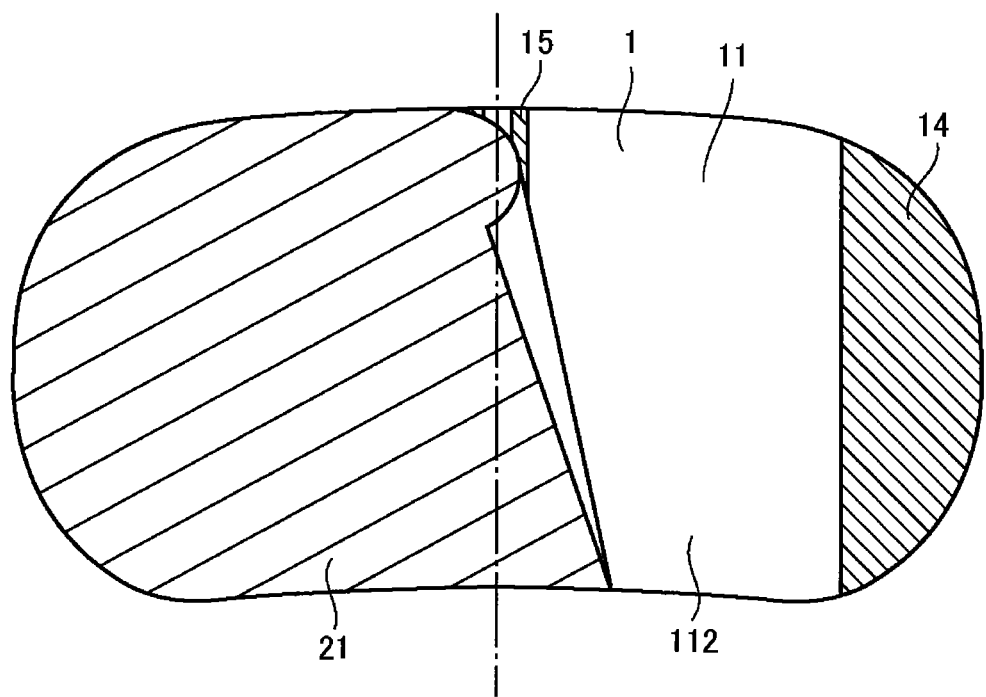
FIG. 7 is a plan view, illustrating a state, in which a release paper is removed from a heating implement.
Figure 8:
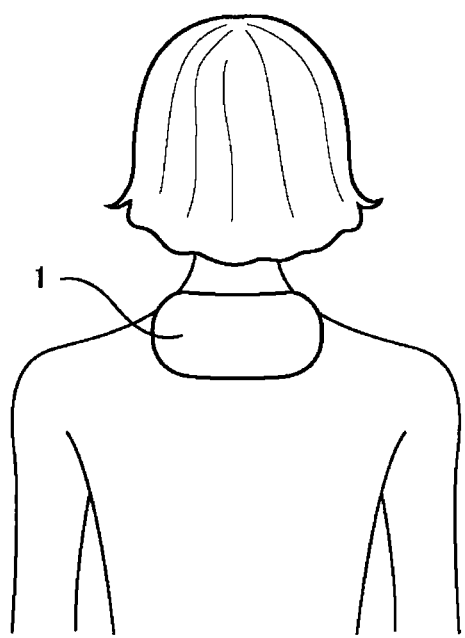
FIG. 8 is a view, illustrating a state, in which a heating implement is put on a wearer.

When the wearer puts on the heating implement 1, the exterior package 3 is opened, and the heating implement 1 is taken out from the exterior package 3. Then, the release paper 2 is removed from the heating implement 1. For example, as shown in FIG. 7, the releasing section 22 is firstly removed from the heating implement 1. Then, one first adhesive layer 14 of the pair of the first adhesive layers 14 is exposed by removing the releasing section 22, and is brought into contact with the skin of the wearer. More specifically, as shown in FIG. 8, the heating implement 1 is disposed on the backside of the neck of the wearer, and the heating implement 1 is adhered on the back side of the neck so that the longitudinal direction of the heating implement 1 elongates in the transverse direction of the wearer. Then, while a part of the heating implement 1 is adhered to the skin, the releasing section 21 is removed from the heating implement 1. Then, the other first adhesive layer 14 of the pair of the first adhesive layers 14, which is exposed by removing the releasing section 21, and the pair of the second adhesive layers 15 are adhered to the skin of the wearer. This achieves fixing the heating implement 1 onto the wearer.

As described above, one of a plurality of releasing sections is removed to expose one of a plurality of adhesive layers, which is fixed to the skin, so that mutual adhesion of the adhesive layers potentially occurred when the heating implement 1 is fixed to the skin can be prevented. Then, the rest of the releasing sections are removed while maintaining the attachment of one adhesive layer to the skin to adhere the adhesive layers of a plurality of adhesive layers except one previously fixed on the skin to the skin, such that the heating implement 1 can be stably adhered to the desired position.

Air enters from a space between the circumference of the first sheet 11 and the skin of the wearer, passes through a space between the first sheet 11 and the skin of the wearer, and proceeds in the inside of the first sheet 11. Eventually, air is supplied to the heating element 13 through the sheet 171 (and the base material layer S, if the base material layer S is provided in the side of the first sheet 11 in the heating element 13). This allows providing desired heat generation characteristics.

In addition to above, since the second sheet 12 of the heating implement 1 is the air-permeable sheet in the present embodiment, air is supplied into the heating implement 1 through the second sheet 12. However, since the sheet 172 of the inner bag 17 is an air-impermeable layer, most of air passing through the second sheet 12 does not reach to the heating element 13, and thus it is significantly difficult to supply air from the side of the second sheet 12 to the heating element 13.

The oxidizeable metal in the heating element 13 is in contact with air to cause oxidization of the oxidizeable metal, and the heating element 13 generates heat. The heating element 13 generates heat to cause evaporation of water in the heating element 13 to generate vapor. Vapor passes through the base material layer S, the sheet 171 and the first sheet 11 (more specifically the exposed region 112B of the first sheet 11) and is released to the outside of the heating implement 1.

In addition to above, if none of the base material layer S is provided in the heating element 13, vapor is released through the sheet 171 and the first sheet 11 to the outside.

On the other hand, since the sheet 172 of the inner bag 17 is the air-impermeable layer, vapor generated in the heating element 13 is blocked by the sheet 172, and almost none of vapor is released from the second sheet 12 to the outside. This allows vapor being preferentially released from the sheet 171, so that vapor can be definitely supplied to the skin of the wearer.

It is apparent that the present invention is not limited to the above described embodiments, and any modifications and improvements without departing from the scope and spirit of the invention are included in the present invention.

For example, while it is described that the sheet 172 is the air-impermeable layer in the above-mentioned embodiment, and for example, any one of the second sheet 12 and the sheet 172 may be the air-impermeable layer, or both may be the air-impermeable layers.

Further, an air-impermeable sheet may be disposed in the inside of the inner bag 17. In this case, the air-impermeable sheet is disposed to be closer to the sheet 172 than the heating element 13. This air-impermeable sheet preferably covers the entire heating element 13 in plan view from the side of the second sheet 12. In such case, the second sheet 12 and the sheet 172 may be the air-impermeable layers, or alternatively may be the air-permeable layers.

Further, while the both ends of the first adhesive layer 14 and the both ends of the second adhesive layer 15 reach to the circumference of the first sheet 11 in plan view from the side of the first sheet in the above-mentioned embodiment, it is not intended to be limited thereto.

For example, the end of the first adhesive layer 14 may not reach to the circumference of the first sheet 11, and a region where the first sheet 11 is exposed may be included between the end of the first adhesive layer 14 and the circumference of the first sheet 11. Similarly, the end of second adhesive layer 15 may not reach to the circumference of the first sheet 11, and a region where the first sheet 11 is exposed may be included between the end of second adhesive layer 15 and the circumference of the first sheet 11. However, in order to stably fix the heating implement 1 to the wearer, an end of at least one of the first adhesive layer 14 and the second adhesive layer 15 in the elongating direction, or preferably ends of both thereof in the elongating direction, preferably reach to the circumference of the aforementioned first sheet 11.

Also, for example, when the end of the first adhesive layer 14 does not reach to the circumference of the first sheet 11, a region enclosed with an extension line of one side of the first adhesive layer 14 in the side of the heating element 13, one side of the second adhesive layer 15 in the side of the heating element 13 and the circumference of the first sheet 11 preferably forms the exposed region 112 that is a region without adhesive layer. Having such configuration, wider area of the exposed region 112 can be ensured.

More specifically, a region enclosed with one side of the first adhesive layer 14 in the side of the heating element or an extension line thereof, one side of the second adhesive layer 15 in the side of the heating element 13 or an extension line thereof, and the circumference of the first sheet 11 preferably forms the exposed region 112 which is region without adhesive layer.

Further, while the first adhesive layer 14 and/or the second adhesive layer 15 do not overlapped with the heating unit 18 in plan view from the side of the first sheet 11 in the above-mentioned embodiment, the configuration is not limited thereto, and the first adhesive layer 14 and/or the second adhesive layer 15 may partially overlap with one side of the heating unit 18 in plan view from the side of the first sheet 11. For example, as shown in FIG. 9, although the heating element 13 does not overlap with the first adhesive layer 14 and/or the second adhesive layer 15, one side of the inner bag 17 of the heating unit 18 may overlap with the second adhesive layer 15. Further, the exposed region 111 may overlap with a part of the heating unit 18, for example, one side of the inner bag 17.

Further, the heating element 13 may overlap with the second adhesive layer 15. More specifically, a part of the heating element 13 may be positioned between the first adhesive layer 14 and the second adhesive layer 15 in plan view from the side of the first sheet 11. However, in view of achieving desired heat generation characteristics of the heating element 13, it is preferable to dispose the second adhesive layer 15 so that a part of the second adhesive layer 15 extends beyond the heating element 13 in the X-axis direction (direction in which the first adhesive layer 14 and the second adhesive layer 15 sandwich the heating element 13) in plan view from the side of the first sheet 11, and in particular, the second adhesive layer 15 is preferably disposed so that the second adhesive layer 15 does not overlap with the heating element 13, similarly as in the above-described embodiment.

Similarly, in view of achieving desired heat generation characteristics of the heating element 13, it is preferable to dispose the first adhesive layer 14 so that a part of the first adhesive layer 14 extends beyond the heating element 13 in the X-axis direction in plan view from the side of the first sheet 11, and in particular, the first adhesive layer 14 is preferably disposed so that the first adhesive layer 14 does not overlap with the heating element 13, similarly as in the above-described embodiment. Further, it is preferable that equal to or higher than 80% of the width of the heating element 13 along the direction in which the first adhesive layer 14 and the second adhesive layer 15 sandwich the heating element 13 (X-axis direction: in the above-mentioned embodiment) is not covered with the adhesive layer, and it is more preferable that from 85 to 95% is not covered with the adhesive layer. It is also preferable that equal to or higher than 80% of the surface area of the heating element 13 does not overlap with the adhesive layer in plan view from the side of the first sheet 11, and it is more preferable that from 85 to 95% of surface area of the heating element 13 does not overlap with the adhesive layer.

While the heating element 13 is housed in the inner bag 17 in the above-mentioned embodiment, it is not essential to provide the inner bag 17. When the inner bag 17 is not provided, the air resistance of the first sheet 11 is preferably equivalent to that of a third sheet (sheet 171) in the case of having the inner bag, and the air resistance of the second sheet 12 is preferably equivalent to that of a fourth sheet (sheet 172) in the case of having the inner bag.

Further, while a clearance is formed between the circumference section 21B of the releasing section 21 and the circumference section 22B of the releasing section 22 in the above-described embodiment, the circumference section 21B may be in contact with the circumference section 22B and no clearance may be made between the circumference sections 21B and 22B.

Still further, a slit may be formed in the heating implement 1 of the above-described embodiment to provide a stretchable configuration in the X-axis direction.

Also, while the heating implement 1 is adhered to the back side of the neck in the above-described embodiment, the configuration is not limited thereto, and it may be adhered to the skin of other site of the wearer.

The fragrance includes, for example, the following components A, and one, two or more of these may be preferably contained. The fragrance may be used as a fragrance composition containing a fragrance component as an active constituent.

[Component (A)]

Linear monoterpene alcohols, sesquiterpene alcohols, acetic acid esters of monoterpene alcohol or alicyclic alcohol, methyl dihydrojasmonate, ionone, or damascone.

Typical linear monoterpene alcohols available here include, for example, geraniol, citronellol, linalool, dihydrolinalool, ethyl linalool, nerol, myrcenol and the like.

Typical sesquiterpene alcohols available here include both linear and cyclic compounds. Typical linear sesquiterpene alcohols available here include, for example, farnesol or nerolidol or the like. Typical cyclic sesquiterpene alcohols available here include, for example, santalol, cedrol, vetivelol (mixture), patchouli alcohol and the like.

Typical acetic acid esters of monoterpene alcohol available here include linalyl acetate, geranyl acetate, citronellyl acetate, ethyl linalyl acetate, lavandulyl acetate, menthanyl acetate and the like. Typical acetic acid esters of alicyclic alcohol include o-tert-butyl cyclohexyl acetate or p-tert-butyl cyclohexyl acetate or the like.

In view of releasing sufficient aroma and ensuring the prevention of the change of aroma during the storage, the content of the component A is preferably equal to or larger than 40% by mass of the total fragrance composition, and is more preferably equal to or larger than 50% by mass, and is further preferably equal to or larger than 60% by mass. When two or more thereof are used, the total contents thereof are preferably equal to or larger than 40% by mass.

Also, as long as the fragrance composition contains the above-described fragrance component as the active constituent, an essential oil may be used. Typical examples of such essential oil includes for example, natural essential oils such as lavender oil, chamomile oil, lavandin oil, rosemary oil and geranium oil and the like.

Still further, in addition to the above-described fragrance component, a solvent may be additionally mixed to the fragrance composition to the extent that provides no interference with the advantageous effects of the present invention. Available solvent includes dipropyleneglycol, ethyldiglycol, isopropylmyristate, benzylbenzoate, triethylcitrate and diethylphthalate and the like.

On the other hand, reduced content of the following fragrance component B, which is a fragrance component other than the above-described fragrance component, is significantly effective, in view of the release of aroma in the use of the heating implement 1 and the prevention of the change of aroma during the storage. In this regard, the content of the following fragrance component B in the fragrance composition is preferably equal to or lower than 50% by mass, and is more preferably equal to or lower than 40% by mass, and is further preferably equal to or lower than 20% by mass, and particularly preferably contains substantially none.

[Component (B)]

Terpene hydrocarbons or aromatic alcohols.

Terpene hydrocarbons include: linear hydrocarbons such as myrcene and farnesene and the like; and cyclic hydrocarbons such as pinene, limonene, camphene, phellandrene, terpinene, terpinolene, p-cymene, cedrene, caryophyllene and the like.

Aromatic alcohol typically includes various types of compounds used as the fragrance components, such as for example, benzyl alcohol, phenylethyl alcohol, pamplefleur (2-methyl-4-phenyl pentanol), dimethylbenzyl carbinol, phenyl hexanol (3-methyl-5-phenyl pentanol) and the like.

When the fragrance composition is prepared, fragrance components described in, for example, "GOSEIKORYO: KAGAKU TO SHOHIN CHISHIKI" (Synthetic perfume chemistry and product knowledge) (authored by Motoichi Indo, Chemical Daily, Tokyo Japan), other than the above-described component A and component B, may be blended to the extent that provides no interference with the advantageous effects of the present invention. More specifically, this includes: aldehydes such as hexyl cinnamic aldehyde, 2-methyl-3-(4-tert-butylphenyl)-propanal, 4-(4-hydroxy-4-methylpentyl)-3-cyclohexene-1-carboxy aldehyde, vanillin and the like; phenols such as anethole, eugenol and the like; and lactones such as γ-nonalactone, γ-undecalactone and the like. The content of the fragrance components that are classified into neither the component A nor the component B is preferably equal to or smaller than 50% by mass in the fragrance composition.

The method to perfume typically includes, for example: a method of directly adding the fragrance composition to a sheet constituting the heating implement 1 by spraying; a method of immersing a sheet with a solvent containing dissolved fragrance composition; or a method of coating a constitutional sheet with a liquid fragrance or a solvent containing dissolved fragrance composition. Furthermore, a method of perfuming powder carrier or oil and fat carrier with a fragrance, and attaching such powder fragrance or paste perfuming product on a sheet may also be adopted.

Concerning the position to be perfumed in the heating implement 1, a liquid fragrance composition may be provided in various positions. In view of successfully releasing aroma of the fragrance composition, it is preferable for the fragrance composition to perfume it to the sheet in a position near the heating element 13. Specifically, the sheets constituting the heating implement 1 include the first sheet 11, the second sheet 12, the sheet 171 and the sheet 172, and in view letting of effectively sensing aroma, the second sheet 12 and the sheet 172 are more preferable, and the sheet 172 is further preferable.

More specifically, the fragrance composition is preferably provided on a fiber sheet or a paper in a material of the sheet 172 constituting the outer surface of the heating unit 18. When the air-impermeable material is laminated in the sheet 172, it is preferable that the perfumed fiber sheet or paper is disposed in the outermost of the heating unit 18. This reduces the influences on the heating element 13, the first adhesive layer 14, or the second adhesive layer 15, so that the deteriorations of the exothermic temperature and the adhesive force due to the storage can be reduced as much as possible. In such case, the type of the paper to which the fragrance composition is provided is not particularly limited, and a general purpose paper produced of wood pulp as a principal raw material can be used. Also, in addition to the paper, a sheet material composed of a fiber material such as nonwoven fabric, fabric cloth and the like, or a sheet having moisture-absorbability and oil-absorbability such as porous film and the like may be employed, provided that the material can be perfumed. In addition to above, it is preferable to perfume the second sheet 12 when the inner bag 17 is not provided as described above. In such case, the second sheet 12 is configured to contain a fiber sheet or a paper, and it is more preferable to perfume the fiber sheet or the paper, and it is further preferable to perfume the paper.

Concerning the using amount of the fragrance composition, mass ratio of the content of the fragrance to the content of the carbon component in the heating implement 1 (fragrance/carbon component) is equal to or higher than 0.2 and equal to or lower than 0.52. This allows sensing aroma upon the use, and obtaining appropriate heat generation characteristics. In view of the heat generation characteristics, it is more preferably equal to or higher than 0.32, and is further preferably equal to or higher than 0.34. On the other hand, in view of the aroma effect, it is more preferably equal to or lower than 0.5, and is further preferably equal to or lower than 0.46. In addition, in view of suitably balancing the aroma, the heat generation characteristics and the adhesive force, it is preferably equal to or higher than 0.32 and equal to or lower than 0.5, and is more preferably equal to or higher than 0.34 and equal to or lower than 0.46.

In addition, the content of the fragrance according to the present invention is the content of the fragrance shortly before using the heating implement 1, and it is not intended to mean the content after the fragrance has volatilized by the use.

The content of the fragrance in the heating implement 1, which also depends on the content of the carbon component in the heating implement 1, is preferably equal to or larger than 0.25 mg/cm$^2$, in view of sensing aroma in the use, and is more preferably equal to or larger than 0.29 mg/cm$^2$, and is further preferably equal to or larger than 0.34 mg/cm$^2$, and on the other hand is preferably equal to or smaller than 0.7 mg/cm$^2$ in view of achieving appropriate heat generation characteristics, and is more preferably equal to or smaller than 0.6 mg/cm$^2$, and is further preferably equal to or smaller than 0.55 mg/cm$^2$.

While a method of measuring the content of the fragrance is not particularly limited, the following method may be employed for the measurements.

The fragrance component is directly extracted from the perfumed heating implement 1 using an organic solvent, and the obtained extract is measured by gas chromatography equipped with a mass spectrometer in a detector to achieve the quantitative analysis. Alternatively, a gas chromatography system equipped with a headspace introduction apparatus may be employed, and the content can be estimated according to a comparison with a calibration curve, which is preliminarily obtained by graphically showing relations of the volatilization volume over the fragrance content.

Against the general tendency that increased content of the fragrance provides deteriorated heat generation characteristics and adhesive force and on the other hand increased content of the carbon component provides insufficient aroma, according to the heating implement 1 of the present invention, the heating implement 1 exhibiting better balance of the aroma, the heat generation characteristics and the adhesive force can be obtained by satisfying the following relations (a) and (b).
(a) a mass ratio of a content of the fragrance to a content of the carbon component in the heating implement 1 (fragrance/carbon component) is equal to or higher than 0.2 and equal to or lower than 0.52; and
(b) the content of the carbon component in the heating implement is equal to or larger than 0.89 mg/cm$^2$.

Further, even if the heating implement 1 of the present invention is adhesively applied to the back of the wearer, the wearer can sense the aroma, since sufficient amount of the fragrance is contained.

Concerning the embodiments as described above, the present invention will further disclose the following compositions, production methods or applications thereof.
<1> A heating implement for body, comprising:
  a first sheet having air-permeability;
  a second sheet;
  a heating element, intermediately arranged between the aforementioned first sheet and the aforementioned second sheet and containing an oxidizeable metal and a carbon component; and
  an adhesive layer provided in one of external surfaces of the aforementioned first sheet which is applied to a wearer side,
  wherein a region without adhesive layer, in which none of the aforementioned adhesive layer is disposed, is provided in at least a part of an external circumference section of the aforementioned first sheet,
  wherein following relations (a) and (b) are satisfied, and
  wherein the heating implement is perfumed with a fragrance:
(a) a mass ratio of a content of the aforementioned fragrance to a content of the aforementioned carbon component in the aforementioned heating implement (fragrance/carbon component) is equal to or higher than 0.2 and equal to or lower than 0.52; and
(b) the content of the aforementioned carbon component in the aforementioned heating implement is equal to or larger than 0.89 mg/cm$^2$.
<2> The heating implement as described in <1>, wherein the aforementioned adhesive layer contains at least one, two or more selected from acrylic-based resins, vinyl acetate-based resins, olefin-based resins and rubber-based resins, and more preferably contains at least one, two or more selected from vinyl acetate-based resins, olefin-based resins and rubber-based resins.

<3> The heating implement as described in <1> or <2>, wherein the aforementioned heating implement is adhesively put to a back of a body of a wearer.

<4> The heating implement as described in any one of <1> to <3>, wherein the heating implement comprises a fiber sheet or a paper perfumed with the aforementioned fragrance between the aforementioned heating element and the aforementioned second sheet or in the aforementioned second sheet.

<5> The heating implement as described in <4>, wherein the paper is preferably perfumed with the aforementioned fragrance.

<6> The heating implement as described in any one of <1> to <5>, wherein the content of the aforementioned fragrance in the aforementioned heating implement is preferably equal to or larger than 0.25 mg/cm$^2$, and is more preferably equal to or larger than 0.29 mg/cm$^2$, and is further preferably, equal to or larger than 0.34 mg/cm$^2$, and on the other hand is preferably equal to or smaller than 0.7 mg/cm$^2$, and is more preferably equal to or smaller than 0.6 mg/cm$^2$, and is further preferably equal to or smaller than 0.55 mg/cm$^2$.

<7> The heating implement as described in any one of <1> to <6>, wherein the aforementioned adhesive layer is provided in a region of the aforementioned first sheet where none of the aforementioned heating unit is disposed in plan view from the side of the aforementioned first sheet.

<8> The heating implement as described in any one of <1> to <7>, wherein the aforementioned heating implement has a horizontally long shape having a longitudinal direction and a width direction perpendicular thereto in plan view.

<9> The heating implement as described in any one of <1> to <8>, wherein the aforementioned heating implement in plan view have a shape in plan view of any of rectangular shape, ellipse shape, oval shape and beans shape.

<10> The heating implement as described in any one of <1> to <9>, wherein the content of the aforementioned carbon component in the aforementioned heating implement is preferably equal to or larger than 0.89 mg/cm$^2$, and is more preferably equal to or larger than 0.96 mg/cm$^2$, and is further preferably equal to or larger than 1.04 mg/cm$^2$.

<11> The heating implement as described in any one of <1> to <10>, wherein the content of the aforementioned carbon component in the aforementioned heating implement is preferably equal to or smaller than 1.63 mg/cm$^2$, and is more preferably equal to or smaller than 1.38 mg/cm$^2$, and is further preferably equal to or smaller than 1.26 mg/cm$^2$.

<12> The heating implement as described in any one of <1> to <11>, wherein a mass ratio of a content of the aforementioned fragrance to a content of the aforementioned carbon component in the aforementioned heating implement (fragrance/carbon component) is equal to or higher than 0.2 and equal to or lower than 0.52, and is preferably equal to or higher than 0.32, and is further preferably equal to or higher than 0.34.

<13> The heating implement as described in any one of <1> to <12>, wherein a mass ratio of a content of the aforementioned fragrance to a content of the aforementioned carbon component in the aforementioned heating implement (fragrance/carbon component) is equal to or higher than 0.2 and equal to or lower than 0.52, and is preferably equal to or lower than 0.5, and is further preferably equal to or lower than 0.46.

<14> The heating implement as described in any one of <1> to <13>, wherein the aforementioned heating element is housed in an inner bag.

<15> The heating implement as described in <14>, wherein the aforementioned inner bag is configured by joining circumference sections of a third sheet disposed in the side of the aforementioned first sheet and a fourth sheet disposed in the side of the aforementioned second sheet.

<16> The heating implement as described in <15>, wherein air resistance of the aforementioned third sheet is preferably equal to or higher than 500 second/100 ml, and is more preferably equal to or higher than 800 second/100 ml, and is further preferably equal to or higher than 1300 second/100 ml, and on the other hand is preferably equal to or lower than 5000 second/100 ml, and is more preferably equal to or lower than 3500 second/100 ml.

<17> The heating implement as described in any one of <14> to <16>, wherein air resistance of the aforementioned the first sheet 11 is preferably equal to or higher than 0 second/100 ml, and is more preferably equal to or higher than 1 second/100 ml, and on the other hand is preferably equal to or lower than 1000 second/100 ml, and is more preferably equal to or lower than 100 second/100 ml, and is further preferably equal to or lower than 10 second/100 ml.

<18> The heating implement as described in any one of <15> to <17>, wherein the aforementioned fourth sheet is an air-impermeable sheet having substantially no air-permeability.

<19> The heating implement as described in any one of <15> to <18>, wherein air-permeability of whole sheet layer comprising the aforementioned second sheet and the aforementioned fourth sheet is lower than air-permeability of whole sheet layer comprising the aforementioned first sheet and the aforementioned third sheet.

<20> The heating implement as described in any one of <1> to <19>, wherein the aforementioned adhesive layer is provided so as to partially overlap with the aforementioned heating element in plan view of the aforementioned heating implement from the side of the aforementioned first sheet.

<21> The heating implement as described in any one of <1> to <20>, wherein the aforementioned adhesive layer includes a pair of first adhesive layers parallelly elongating in a single direction and being spaced apart from each other, and a second adhesive layer disposed in a region between a pair of the aforementioned first adhesive layers and elongating in the same direction following the first adhesive layers.

<22> The heating implement as described in <21>, wherein the aforementioned heating element is positioned in an exposed region that is the aforementioned region without adhesive layer formed between the aforementioned first adhesive layer and the aforementioned second adhesive layer in plan view of the aforementioned heating implement.

<23> The heating implement as described in any one of <1> to <22>, wherein a release paper covering the aforementioned adhesive layer is provided.

<24> The heating implement as described in <23>, wherein the aforementioned release paper is composed of at least a pair of releasing sections, and one of the aforementioned releasing sections covers one first adhesive layer of the aforementioned pair of first adhesive layers and a pair of the aforementioned second adhesive layers, and the other of the aforementioned releasing sections covers the other first adhesive layer of the aforementioned pair of the first adhesive layers.

<25> The heating implement as described in <24>, wherein the aforementioned pair of releasing sections are located spaced apart from each other in plan view of the aforementioned heating implement from the side of the aforementioned the first sheet.

<26> The heating implement as described in any one of <21> to <25>, wherein the aforementioned second adhesive layer is provided in vicinity of a vertical center line of the aforementioned heating implement.

<27> The heating implement as described in any one of <21> to <25>, wherein a plurality of the aforementioned second adhesive layers are provided, and the aforementioned plurality of second adhesive layers are located spaced apart from each other to form a region without adhesive layer, in which none of the aforementioned adhesive layer is present.

<28> The heating implement as described in <27>, wherein the aforementioned plurality of second adhesive layers are arranged in symmetric positions across a vertical center line of the aforementioned heating implement.

<29> The heating implement as described in <28>, wherein the aforementioned vertical center line is a folding line for the aforementioned heating implement, and none of the aforementioned adhesive layer is present on the folding line.

<30> The heating implement as described in any one of <1> to <29>, wherein the aforementioned adhesive layer contains an adhesive basis, a tackifying resin and a softening agent as constituent components.

<31> The heating implement as described in any one of <1> to <30>, wherein the aforementioned heating implement is adhesively put to any of a back side of a neck, a section from a back side of a neck to a shoulder, a back, and an abdomens of a body of a wearer.

<32> A method of using the heating implement as described in any one of <1> to <31> by adhesively attaching thereof to a body.

<33> A method of obtaining a fragrance component by using the heating implement as described in any one of <1> to <31>.

EXAMPLES

Next, Examples of the present invention will be described.

Example 1

<Preparation of Heating Implement 1>

The heating implement 1 shown in FIG. 1 and FIG. 10 was produced as described below.

[Production of Exothermic Powder-Water Dispersion]

100 parts by mass of an oxidizeable metal, 8 parts by mass of a carbon component, 62 parts by mass of water, 11 parts by mass of a reaction accelerator, and 0.2 parts by mass of a thickener were prepared, and were produced in the next procedure. The thickener was dissolved in water, and then the reaction accelerator was dissolved therein to prepare an aqueous solution, and on the other hand a pre-mixed powder of an oxidizeable metal and a carbon component was prepared, and then the pre-mixed powder was added to the aqueous solution, and the solution was stirred at 150 rpm for 10 minutes to obtain a slurry-like exothermic powder-water dispersion.

Types, product names and manufacturers of the oxidizeable metal, the carbon component, water, the reaction accelerator, and the thickener are as follows.

Oxidizeable metal: iron powder (Iron powder RKH, Mean particle diameter 45 μm, commercially available from DOWA IP Creation Co., Ltd.)

Carbon component: Activated carbon (CARBORAFFIN, Mean particle diameter 40 μm, commercially available from Japan Enviro Chemicals, Ltd.)

Water: Tap water

Reaction accelerator: Sodium chloride (Japanese Pharmacopoeia sodium chloride, commercially available from Otsuka Chemical Co., Ltd.)

Thickener: Xanthan gum (Echogum BT, commercially available from DSP GOKYO FOOD & CHEMICAL Co., Ltd.)

[Production of Heating Element 13]

A polymeric sheet (air resistance: 1 second/100 ml) was used as the base material layer S, which was made by laminating paper A made of wood pulp (20 g/m$^2$, commercially available from Inokami Co., Ltd.), water absorbent polymer (sodium polyacrylate, spherical, mean particle diameter 300 μm, 50 g/m$^2$, AQUALIC CA, commercially available from NIPPON SHOKUBAI Co., Ltd.) and paper B made of wood pulp (30 g/m$^2$, commercially available from Inokami Co., Ltd.) in this order. An air-impermeable polyethylene sheet (grammage: 27 g/m$^2$) was prepared as the base material layer R, and the base material layer R of 25 cm$^2$ (5 cm×5 cm), which is the size of a single cell, was coated with the above-described exothermic powder-water dispersion over the range of 25 cm$^2$ (5 cm××5 cm) at 1.4 to 1.9 g/25 cm$^2$ by 0.1 g/25 cm$^2$ increments as shown in Table 1, and the resultant products were laminated in a manner, in which the side of the paper B of the base material layer S faced the coated surface, to obtain the heating element 13. In addition, the amount (mg/cm$^2$) of the activated carbon for the heating implement 1 as will be discussed later is shown in Table 1.

[Production of Heating Unit 18]

The heating element 13 was put in the inside of the inner bag 17, which was composed of the sheet 171 (air resistance 1,700 second/100 ml) and the sheet 172 (air-impermeable sheet), and the circumference portion was hermetically sealed. At this time, the heating element 13 was arranged so that the side of the base material layer S side was positioned in the side of the sheet 171 (air-permeable side). The heating unit 18 was obtained by the above procedure.

The sheet 172 (air-impermeable sheet) was produced by laminating (not shown) a PE sheet (35 g/m$^2$) and a paper made of wood pulp (35 g/m$^2$), and was thermally sealed with the sheet 171 in the side of the above-described PE sheet. A perfumed paper with a fragrance in the range of from 0.297 to 0.668 mg/cm$^2$ with respect to the heating implement 1 as will be discussed later as shown in Table 1 was employed as the paper, and was disposed so that the paper was situated outside of the heating unit 18. A fragrance containing lavender oil (the aforementioned component A was the main constituent) at the content of 77% by mass was used (the aforementioned component B: 0% by mass). Table 1 show the mass ratios of the fragrance/activated carbon of 42 samples, which consists of the heating elements 13 with 6 different amounts of coating of the above-described exothermic powder-water dispersion per unit cell perfumed with 7 different perfuming amounts, respectively (including non-perfuming article).

[Production of Heating Implement 1]

A needle-punched nonwoven fabric (air resistance: equal to or smaller than 1 second/100 ml, grammage: 80 g/m$^2$) was employed as the first sheet 11, and a spunbonded nonwoven fabric (air resistance: equal to or smaller than 1 second/100 ml, grammage: 38 g/m$^2$) was employed as the second sheet 12. Then, two heating units 18 were arranged spaced apart from each other in the inside of the first sheet 11 and the second sheet 12 (2-cell arrangement). Then, the circumference portions of the first sheet 11 and the second sheet 12 were hermetically sealed.

Further, the first adhesive layer 14 and the second adhesive layer 15 were arranged as in the arrangement shown in FIG. 1. A rubber-based adhesive agent was employed, and the outer surface of the first sheet 11 was applied with such adhesive agent to provide the first adhesive layer 14 and the second adhesive layer 15. Total area of the adhesive areas of the first adhesive layer 14 and the second adhesive layer 15 was 36 cm$^2$, and the total amount of the adhesive agent was 0.63 g. Area in plan view of the whole the heating implement 1 after the production was 134.8 cm$^2$.

The obtained heating implement 1 was put in an airtight container (aluminum pillow) having oxygen barrier property, and was stored at 50 degrees C. for 3 days, and then was taken out and was further stored in 50% RH environment at 20 degrees C. for 3 hours, and then the evaluations shown below were conducted.

Table 1
[Mass Ratio: Fragrance/Activated Carbon]

TABLE 1

[Mass Ratio: Fragrance/Activated Carbon]

| | Coating Amount of Exothermic Powder-Water Dispersion (g/cell) | | | | | |
|---|---|---|---|---|---|---|
| | 1.4 | 1.5 | 1.6 | 1.7 | 1.8 | 1.9 |
| Amount of Activated Carbon (mg/cm$^2$) | 0.948 | 1.016 | 1.084 | 1.151 | 1.219 | 1.287 |
| Perfuming Amount (mg/cm$^2$) 0.000 | 0.000 | 0.000 | 0.000 | 0.000 | 0.000 | 0.000 |
| 0.297 | 0.313 | 0.292 | 0.274 | 0.258 | 0.243 | 0.231 |
| 0.378 | 0.399 | 0.372 | 0.349 | 0.329 | 0.310 | 0.294 |
| 0.445 | 0.469 | 0.438 | 0.411 | 0.387 | 0.365 | 0.346 |
| 0.512 | 0.540 | 0.504 | 0.472 | 0.445 | 0.420 | 0.398 |
| 0.579 | 0.610 | 0.570 | 0.534 | 0.503 | 0.475 | 0.450 |
| 0.668 | 0.704 | 0.657 | 0.616 | 0.580 | 0.548 | 0.519 |

[Evaluations]

Respective heating implements 1 shown in the above-described Table 1 were evaluated as follows, and the results were shown in Tables 2 to 6.

[Measurement of Exothermic Temperature]

The exothermic measurements were conducted with a measuring apparatus in conformity with JIS-S4100, where an adhesive face of the heating implement 1 was adhered to a measuring surface of the measuring apparatus. Average values (degrees C.) of the maximum temperatures for 10 measurements are shown in Table 2 as the evaluation items of the exothermic temperature. It was determined that better thermal sense was obtained when the average value of the maximum temperature was within the range of from 53 to 57 degrees C., in particular within the range of from 54 to 56 degrees C.

TABLE 2

[Heat Generation Characteristic of Heating Implement (Maximum Temperature [° C.])]

| | Coating Amount of Exothermic Powder-Water Dispersion (g/cell) | | | | | |
|---|---|---|---|---|---|---|
| | 1.4 | 1.5 | 1.6 | 1.7 | 1.8 | 1.9 |
| Amount of Activated Carbon (mg/cm$^2$) | 0.948 | 1.016 | 1.084 | 1.151 | 1.219 | 1.287 |
| Perfuming Amount (mg/cm$^2$) 0.000 | 55.1 | 55.8 | 55.6 | 57.3 | 58.0 | |
| 0.297 | | 54.6 | 55.6 | 55.8 | | |
| 0.378 | 53.1 | 54.3 | 55.0 | 55.0 | 55.4 | |
| 0.445 | 52.3 | 53.8 | 55.1 | 55.5 | 55.2 | |
| 0.512 | | 53.9 | 54.8 | 54.7 | 55.3 | |
| 0.579 | | 52.4 | 54.1 | | | |
| 0.668 | | 52.0 | 53.5 | | | |

[Evaluations of Release of Aroma and Change of Aroma]

Three panelists specialized in aroma sensed aromas of the heating implements 1 of test products, and evaluated the quantitative changes as "Release of Aroma" by 7 steps of absolute scales from 0 to 6, and also evaluated the qualitative changes as "Change of Aroma" by 4 steps of absolute scales from 0 to 3, and the respective evaluations were averaged. In addition to above, when the change of aroma was considerable, the state of the change was discussed in a specialized panel. The results are shown in Tables 3 and 4. Concerning the release of aroma, steps 2 to 4 are preferable, and 2.5 to 3 are more preferable.

<Criterion for Evaluation of Release of Aroma: Seven Step-Absolute Scale>

0: Unscented

1: Minimally sensed

2: Weakly sensed

3: Clearly sensed

4: Strongly sensed

5: Very strongly sensed

6: Most strongly sensed

<Criterion for Evaluation of Change of Aroma: Four Step-Absolute Scale>

0: Totally no change

1: Almost no change

2: Small change

3: Considerable change

TABLE 3

[Evaluation of Release of Aroma (7 Steps)]

| | Coating Amount of Exothermic Powder-Water Dispersion (g/cell) | | | | | |
|---|---|---|---|---|---|---|
| | 1.4 | 1.5 | 1.6 | 1.7 | 1.8 | 1.9 |
| Amount of Activated Carbon (mg/cm$^2$) | 0.948 | 1.016 | 1.084 | 1.151 | 1.219 | 1.287 |
| Perfuming Amount (mg/cm$^2$) 0.000 | 0 | 0 | 0 | 0 | 0 | 0 |
| 0.297 | 2.0 | 2.0 | 1.7 | 1.7 | 1.0 | 1.0 |
| 0.378 | 3.0 | 3.0 | 2.7 | 2.7 | 2.0 | 2.0 |
| 0.445 | 3.0 | 3.0 | 3.0 | 3.0 | 2.7 | 2.8 |
| 0.512 | 3.0 | 3.0 | 3.0 | 3.0 | 3.0 | 3.0 |
| 0.579 | 3.7 | 3.3 | 3.0 | 3.0 | 3.0 | 3.0 |
| 0.668 | 4.0 | 4.0 | 3.7 | 3.7 | 3.3 | 3.0 |

TABLE 4

[Evaluation of Change of Aroma (4 Steps)]

| | | Coating Amount of Exothermic Powder-Water Dispersion (g/cell) | | | | | |
|---|---|---|---|---|---|---|---|
| | | 1.4 | 1.5 | 1.6 | 1.7 | 1.8 | 1.9 |
| Amount of Activated Carbon (mg/cm$^2$) | | 0.948 | 1.016 | 1.084 | 1.151 | 1.219 | 1.287 |
| Perfuming Amount (mg/cm$^2$) | 0.000 | 0 | 0 | 0 | 0 | 0 | 0 |
| | 0.297 | 0.3 | 0.3 | 0.3 | 0.3 | 0.3 | 0.3 |
| | 0.378 | 0.3 | 0.3 | 0.3 | 0.3 | 0.3 | 0.3 |
| | 0.445 | 0.3 | 0.3 | 0.3 | 0.3 | 0.3 | 0.3 |
| | 0.512 | 0.3 | 0.3 | 0.3 | 0.3 | 0.3 | 0.3 |
| | 0.579 | 0.3 | 0.3 | 0.3 | 0.3 | 0.3 | 0.3 |
| | 0.668 | 0.3 | 0.3 | 0.3 | 0.3 | 0.3 | 0.3 |

[Evaluation of Adhesive Force]

Figure 11:
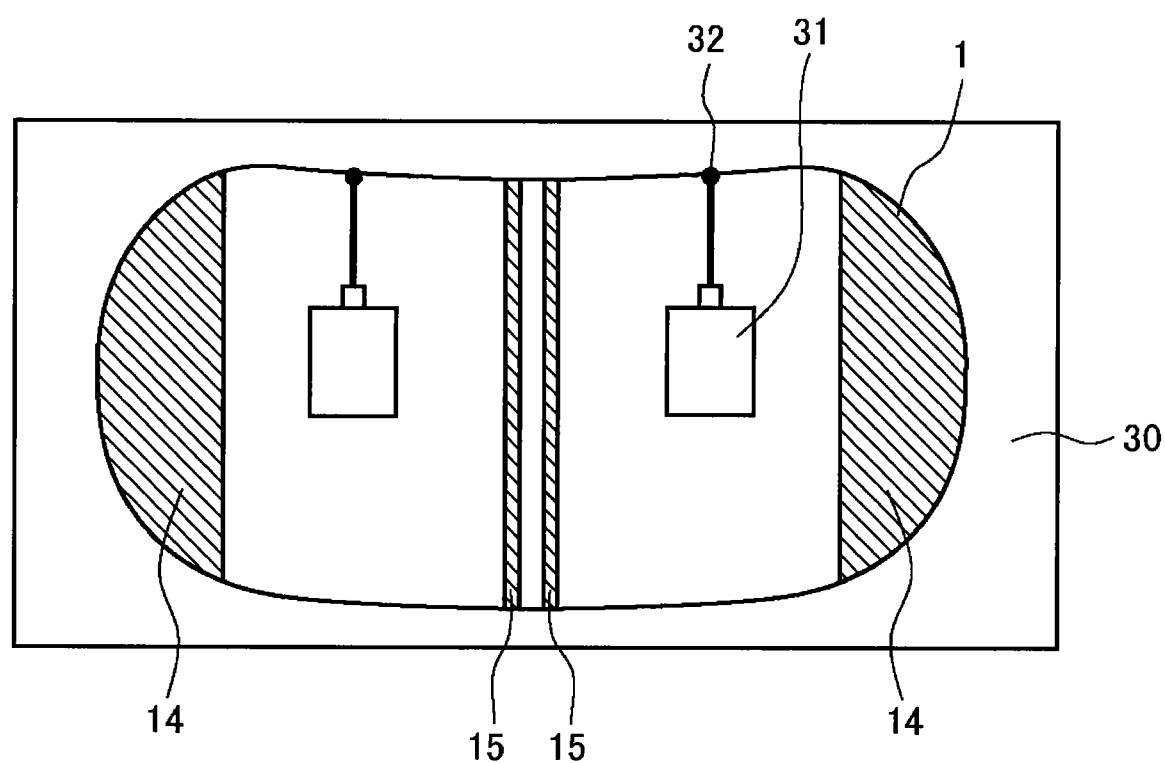
FIG. 11 is a schematic plan view, useful in describing a method for measuring adhesive force of a heating implement.

The measurements of the adhesive force were conducted in a constant temperature room of 20+/−2 degrees C. and 50+/−15%. As shown in FIG. 11, a stainless steel board 30 (A4 size) having clean and smooth surface was prepared, and the surface thereof was wiped with Elleair Prowipe (DAIO PAPER CORPORATION) impregnated with ethanol, and then was dry-wiped with Elleair Prowipe. The heating implement 1 (sheet) was taken out from the packaging bag, and the sheet was picked up without touching any section of the first adhesive layer 14 and the second adhesive layer 15, and then the sheet was spread and quietly placed on a stainless steel board 30 that was horizontally placed. A side of a weight of 200 g was held, and sections of the first adhesive layer 14 and the second adhesive layer 15 were compressed twice while rubbing thereof over the sheet. The stainless steel board 30 was immediately and vertically mounted to a wall so that a convex section of the sheet was on the lower side in two-dimensional view, and was allowed to stand for 1 minute. A weight 31 of 100 g was connected to a tip of a handle of clip 32 (alligator clip CP-106: Plus Stationery Co., Ltd., 1 mm-thick silicone piece was placed on clip face for anti-slippage) with a kite string, and two of such clip with weight were prepared. The clips 32 with the weight 31 were oriented so that the handle that connected the kite string was placed in the side of the stainless steel board 30, and were attached to upper two sites of the sheet (located on the same line as the heating element, and sections without application of the first adhesive layer 14 and the second adhesive layer 15) (FIG. 11). At this time, while the weight 31 was supported with one hand, the hand was slowly lowered, and the time commencing the measurement was determined as the time when a load of the weight 31 was started to be applied on the sheet. The time taken until the sheet was removed off the stainless steel board 30 (average value of time in seconds taken until the left side was removed and time in seconds taken until the right side was removed) was measured, and the results are shown in Table 5, and the evaluations were carried out as follows.

Good: equal to or longer than 82 seconds

Moderately good: longer than 80 seconds and shorter than 82 seconds

Not good: equal to or shorter than 80 seconds

TABLE 5

[Evaluation of Adhesive Force (sec.)]

| | | Coating Amount of Exothermic Powder-Water Dispersion (g/cell) | | | | | |
|---|---|---|---|---|---|---|---|
| | | 1.4 | 1.5 | 1.6 | 1.7 | 1.8 | 1.9 |
| Amount of Activated Carbon (mg/cm$^2$) | | 0.948 | 1.016 | 1.084 | 1.151 | 1.219 | 1.287 |
| Perfuming Amount (mg/cm$^2$) | 0.000 | 108.5 | 109.0 | 110.0 | 109.0 | 109.3 | |
| | 0.297 | 91.0 | 91.0 | 92.5 | 92.0 | 92.8 | |
| | 0.378 | 92.8 | 91.7 | 90.3 | 90.0 | 89.5 | |
| | 0.445 | 79.0 | 82.2 | 86.0 | 87.1 | 89.0 | |
| | 0.512 | 80.0 | 80.9 | 81.7 | 82.9 | 84.0 | |
| | 0.579 | 79.1 | 79.4 | 79.6 | 80.0 | 81.0 | |
| | 0.668 | 76.0 | | 72.8 | | 75.5 | |

In addition, concerning the above-described time of the evaluation for the adhesive force for 6 types of the heating implements 1 containing different amounts of activated carbon, ratio of the time for the respective perfuming articles to the time of perfuming amount of 0 g/cell are respectively shown in Table 6, and the evaluations were carried out as follows.

Good: equal to or higher than 0.75

Moderately good: higher than 0.74 and lower than 0.75

Not good: equal to or lower than 0.74

TABLE 6

[Evaluation of Adhesive Force (ratio of time in second to non-perfumed product)]

| | | Coating Amount of Exothermic Powder-Water Dispersion (g/cell) | | | | | |
|---|---|---|---|---|---|---|---|
| | | 1.4 | 1.5 | 1.6 | 1.7 | 1.8 | 1.9 |
| Amount of Activated Carbon (mg/cm$^2$) | | 0.948 | 1.016 | 1.084 | 1.151 | 1.219 | 1.287 |
| Perfuming Amount (mg/cm$^2$) | 0.000 | 1.000 | 1.000 | 1.000 | 1.000 | 1.000 | |
| | 0.297 | 0.893 | 0.835 | 0.840 | 0.844 | 0.849 | |
| | 0.378 | 0.856 | 0.841 | 0.821 | 0.826 | 0.819 | |
| | 0.445 | 0.728 | 0.754 | 0.782 | 0.799 | 0.814 | |
| | 0.512 | 0.737 | 0.742 | 0.742 | 0.760 | 0.768 | |
| | 0.579 | 0.729 | 0.729 | 0.724 | 0.734 | 0.741 | |
| | 0.668 | 0.700 | | 0.662 | | 0.691 | |

Example 2

<Production of Heating Implement 2>

A heating implement 2 was produced by the similar operations as in Example 1, except that the amount per cell of the exothermic powder-water dispersion for coating on the base material layer R in the above "Production of Heating Element 13" in Example 1 was changed to 1.6 g/25 cm$^2$, the perfuming amount of the fragrance in the above Example 1 "Production of Heating Unit 18" was changed to 0.445 mg/cm$^2$, and the sheet 171 was substituted with that having air resistance as shown in Table 7.

[Evaluation of Heating Implement 2]

The exothermic measurements were conducted for the produced heating implements 2, according to the method described in the above-described "Measurement of Exothermic Temperature". The results are shown in Table 7. In addition to above, all of the results of evaluations for "Release of Aroma," "Change of Aroma" and "Adhesive Force" were equivalent to the evaluation results for the same activated carbon amounts and perfuming amounts in Example 1 (Tables 3 to 6).

TABLE 7

[Exothermic Characteristic versus Air Resistance of Sheet in Heating Implement]

| Air Resistance of Sheet 171 (second/100 ml) | Maximum Temperature [° C.] |
|---|---|
| 600 | 55.5 |
| 1000 | 56.4 |
| 1300 | 56.0 |
| 3500 | 54.4 |
| 5000 | 53.4 |

Example 3

[Production of Exothermic Powder]

Iron powder, activated carbon, tap water and sodium chloride used in the above-described "Production of Exothermic Powder-Water Dispersion" in Example 1, and water absorbent polymer used in the above-described "Production of Heating Element 13," were employed to produce the exothermic powders according to the following procedure.

First of all, 100 parts by mass of the iron powder, 14.1 parts by mass of the water absorbent polymer and 8 parts by mass of the activated carbon were mixed, and then 73 parts by mass of 15.1% salt solution by mass was mixed thereto in nitrogen atmosphere to produce the exothermic powder.

<Production of Heating Implement 3>

The heating implement 3 was produced by similar procedure except that, in place of the heating element 13 in "Production of Heating Unit 18" of the above-described Example 1, 1.725 g of the exothermic powder obtained in the above section was put in the inner bag 17 that was adjusted to have the inside dimension of 5 cm×5 cm and was perfumed in nitrogen atmosphere. The amount of the activated carbon in the produced heating implement 3 was 1.084 mg/cm$^2$, and the perfuming amount was 0.445 mg/cm$^2$.

[Evaluation of Heating Implement 3]

Evaluations of "Heat generation characteristic," "Release of Aroma" and "Change of Aroma" and evaluation of "Adhesive Force" for the above-described obtained heating implement 3 were conducted, and the following results were obtained.

Heat generation characteristic (maximum temperature): 53.7 degrees C.
Evaluation of release of aroma (7 steps): 3.0
Evaluation of change of aroma (4 steps): 0.3
Evaluation of adhesive force (second): 87.0 seconds
Evaluation of adhesive force (ratio of time in seconds to the non-perfumed product): 0.791.

Example 4

<Production of Heating Implement 4>

A heating implement 4 was produced by the similar operations as in Example 1, except that the amount per cell of the exothermic powder-water dispersion for coating on the base material layer R in the above "Production of Heating Element 13" in Example 1 was changed to 1.6 g/25 cm$^2$, the perfuming amount of the fragrance in the above Example 1 "Production of Heating Unit 18" was changed to 0.445 mg/cm$^2$, and the second adhesive layers 15 in "Production of Heating Implement 1" in the above-described Example 1 were arranged as shown in FIG. 12. In addition to above, the total area of the second adhesive layers 15 was identical to that in Example 1.

[Evaluation of Heating Implement 4]

Evaluations of "Heat generation characteristic," "Release of Aroma" and "Change of Aroma" and evaluation of "Adhesive Force" for the above-described obtained heating implement 4 were conducted, and the following results were obtained.

Heat generation characteristic (maximum temperature): 55.2 degrees C.
Evaluation of release of aroma (7 steps): 3.0
Evaluation of change of aroma (4 steps): 0.3
Evaluation of adhesive force (second): 108 seconds
Evaluation of adhesive force (ratio of time in seconds to the non-perfumed product): 0.98

Comparative Example 1

<Production of Heating Implement 5>

A heating implement 5 was produced by the similar operations as in Example 1, except that the amount of the carbon component over 100 parts by mass of the oxidizeable metal was changed to 6 parts by mass and the amount of water was changed to 55 parts by mass in "Production of Exothermic Powder-Water Dispersion" of the above-described Example 1, and the amount per cell of the exothermic powder-water dispersion for coating on the base material layer R in the above "Production of Heating Element 13" in Example 1 was changed to 1.4 g/25 cm$^2$. The amount of the activated carbon in the heating implement 3 was 0.75 mg/cm$^2$, and the fragrance/activated carbon mass ratio was 0.593.

[Evaluation of Heating Implement 5]

Evaluations of "Heat generation characteristic," "Release of Aroma" and "Change of Aroma" and evaluation of "Adhesive Force" for the produced heating implement 5 were conducted, and the following results were obtained. In this case, since the results of both "Heat generation characteristic" and "Adhesive Force" were poor, the evaluation of aroma was not conducted.

Heat generation characteristic (maximum temperature): 49.3 degrees C.
Evaluation of adhesive force (second): 79 seconds This application claims priority based on Japanese Patent Application No. 2013-121,733 filed Jun. 10, 2013, entire disclosures of which are hereby incorporated by reference.

The invention claimed is:

1. A heating implement for a body, comprising:
 a first sheet, which is air-permeable;
 a second sheet;
 a heating element, present between said first sheet and said second sheet, said heating element comprising an oxidizeable metal and a carbon component; and
 an adhesive layer at least partially covering an external surface of said first sheet,
 wherein said first sheet has a first region in which said adhesive layer is not present, said first region being located in at least a part of an external circumference section of said first sheet,
 wherein the heating implement comprises a fragrance,
 wherein relations (a) and (b) are satisfied:
 (a) a mass ratio of a content of said fragrance to a content of said carbon component is from 0.32 to 0.52; and
 (b) the amount of said carbon component in said heating implement is from 0.89 to 1.63 mg/cm$^2$,
 wherein the content of said fragrance includes a Component A,
 wherein the Component A is greater than or equal to 40% by mass of a total composition of the content of said fragrance, and wherein the Component A is one of a linear monoterpene alcohol, a sesquiterpene alcohol, an acetic acid ester of monoterpene alcohol or alicyclic alcohol, methyldihydrojasmonate, ionone, or damascene.

2. The heating implement according to claim 1, wherein said heating implement comprises a fiber sheet or a paper comprising said fragrance between said heating element and said second sheet or in said second sheet.

3. The heating implement according to claim 2, wherein said heating implement comprises the paper comprising said fragrance between said heating element and said second sheet or in said second sheet.

4. The heating implement according to claim 1, wherein said heating element is present in an inner bag, which is present between said first sheet and said second sheet.

5. The heating implement according to claim 4, wherein said inner bag is configured by joining circumference sections of a third sheet disposed in a side of said first sheet and a fourth sheet disposed in a side of said second sheet.

6. The heating implement according to claim 5, wherein an air-permeability of said third sheet is equal to or lower than 5,000 second/100 ml.

7. The heating implement according to claim 5, wherein said fourth sheet is a sheet having substantially no air-permeability.

8. The heating implement according to claim 5, wherein an air-permeability of a whole sheet layer comprising said second sheet and said fourth sheet is lower than an air-permeability of a whole sheet layer comprising said first sheet and said third sheet.

9. The heating implement according to claim 1, wherein said adhesive layer comprises at least one member selected from the group consisting of an acrylic-based resin, a vinyl acetate-based resin, an olefin-based resin, and a rubber-based resin.

10. The heating implement according to claim 1,
wherein said adhesive layer is present in a second region of said first sheet where none of said heating element is present in a plan view from a side of said first sheet, and
wherein said adhesive layer includes an amount of adhesive coating from 140 $g/m^2$ to 220 $g/m^2$.

11. The heating implement according to claim 1,
wherein said adhesive layer partially overlaps with said heating element in a plan view of said heating implement from a side of said first sheet, and
wherein said adhesive layer includes an amount of adhesive coating from 140 $g/m^2$ to 220 $g/m^2$.

12. The heating implement according to claim 1, wherein said adhesive layer includes:
a pair of first adhesive layers, aligned parallel to each other and in a single direction and being spaced apart from each other, and
a second adhesive layer present in a region between said pair of first adhesive layers and aligned in the same direction of said pair of first adhesive layers.

13. The heating implement according to claim 12, wherein said heating element is in an exposed region, which is in said first region in which said adhesive layer is not present, between one of the first adhesive layers of said pair of first adhesive layers and said second adhesive layer in a plan view of said heating implement.

14. The heating implement according to claim 1, wherein the relations (a) and (b) are set to allow volatilization effect of said heating element on said fragrance while inhibiting deterioration of adhesive force of adhesive of said adhesive layer and exothermic temperature of said heating element due to adsorption of said fragrance by the adhesive and said carbon component.

15. The heating implement according to claim 14,
wherein said adhesive layer includes a pair of first adhesive layers, and a pair of second adhesive layers, and
wherein a release paper is comprised of at least a pair of releasing sections, one of said releasing sections covers one first adhesive layer of said pair of first adhesive layers and the pair of said second adhesive layers, and the other of said releasing sections covers the other first adhesive layer of said pair of the first adhesive layers.

16. The heating implement according to claim 12, wherein said second adhesive layer is present in a vicinity of a vertical center line of said heating implement extending in a transverse direction.

17. The heating implement according to claim 12, wherein said second adhesive layer includes a plurality of second adhesive layers, and each said second adhesive layer of said plurality of second adhesive layers is spaced apart from each other to form said first region in which said adhesive layer is not present.

18. The heating implement according to claim 17, wherein each said second adhesive layer of said plurality of second adhesive layers is arranged in symmetric positions on opposite sides of a vertical center line of said heating implement that extends in a transverse direction.

19. The heating implement according to claim 18, wherein said vertical center line is a folding line for said heating implement, and no adhesives of said plurality of second adhesive layers are present on the folding line.

20. The heating implement according to claim 12, wherein said first region in which said adhesive layer is not present is in an entirety of a section between one first adhesive layer of said pair of first adhesive layers and said second adhesive layer.

* * * * *